(12) United States Patent
Hodko et al.

(10) Patent No.: US 11,609,472 B2
(45) Date of Patent: Mar. 21, 2023

(54) ELECTROPHORETIC CHIP FOR ELECTROPHORETIC APPLICATIONS

(71) Applicant: ADOR DIAGNOSTICS S.R.L., Rome (IT)

(72) Inventors: Dalibor Hodko, Poway, CA (US); Howard R. Reese, Poway, CA (US); Vladimir Hurgin, Ashdod (IL)

(73) Assignee: ADOR DIAGNOSTICS S.R.L., Rome (IT)

( * ) Notice: Subject to any disclaimer, the term of this patent is extended or adjusted under 35 U.S.C. 154(b) by 932 days.

(21) Appl. No.: 16/473,108

(22) PCT Filed: Dec. 28, 2017

(86) PCT No.: PCT/IL2017/051403
§ 371 (c)(1),
(2) Date: Jun. 24, 2019

(87) PCT Pub. No.: WO2018/122856
PCT Pub. Date: Jul. 5, 2018

(65) Prior Publication Data
US 2019/0361313 A1    Nov. 28, 2019

(30) Foreign Application Priority Data

Dec. 29, 2016 (IL) .......................................... 249856
Dec. 29, 2016 (IL) .......................................... 249857

(51) Int. Cl.
*G02F 1/167* (2019.01)
*C40B 30/10* (2006.01)
(Continued)

(52) U.S. Cl.
CPC ........ *G02F 1/167* (2013.01); *B01L 3/502753* (2013.01); *C12N 15/1013* (2013.01);
(Continued)

(58) Field of Classification Search
CPC ............... G02F 1/167; B01L 3/502707; B01L 3/50273; B01L 3/502753; B01L 7/525; B01L 2200/0652; B01L 2300/043
See application file for complete search history.

(56) References Cited

U.S. PATENT DOCUMENTS 6,372,813 B1    4/2002  Johnson et al.
6,686,150 B1    2/2004  Blackburn et al.
(Continued)

FOREIGN PATENT DOCUMENTS

CN      1376779 A    10/2002
CN    102037351 A     4/2011
(Continued)

OTHER PUBLICATIONS

European Search Report dated May 25, 2020, which issued during the prosecution of Applicant's European App No. 17886778.4.
(Continued)

*Primary Examiner* — Roy P Rabindranath
(74) *Attorney, Agent, or Firm* — Sughrue Mion, PLLC

(57) ABSTRACT

The present invention discloses an electrophoretic chip comprising: (a) a non-conductive substrate designed to support elements of said electrophoretic chip; (b) an electrode structure for conducting current through said electrophoretic chip, printed on said non-conductive substrate and comprising a counter electrode and at least one working electrode, each electrode comprising a conductive low-resistance ink layer printed on the non-conductive substrate, and a carbon ink layer printed on top of and fully or partially covering said conductive low-resistance ink layer; (c) a dielectric ink insulator layer placed on top of, and covering, said electrode structure, said dielectric ink insulator layer having at least one opening above the counter electrode and at least one opening above said at least one working electrode, thereby forming at least one addressable location; and (Continued)

(d) a molecule capturing matrix spotted on and covering said at least one addressable location, thereby creating at least one microgel region.

20 Claims, 22 Drawing Sheets

(51) Int. Cl.
*B01L 3/00* (2006.01)
*C12N 15/10* (2006.01)
*B01L 7/00* (2006.01)
*C12M 1/00* (2006.01)
*C40B 40/00* (2006.01)

(52) U.S. Cl.
CPC ........... *C40B 30/10* (2013.01); *B01L 3/50273* (2013.01); *B01L 3/502707* (2013.01); *B01L 7/525* (2013.01); *B01L 2200/0652* (2013.01); *B01L 2300/043* (2013.01); *B01L 2300/044* (2013.01); *B01L 2300/0645* (2013.01); *B01L 2300/0672* (2013.01); *B01L 2300/0816* (2013.01); *B01L 2300/0861* (2013.01); *B01L 2300/0864* (2013.01); *B01L 2400/0478* (2013.01); *C12M 1/00* (2013.01); *C40B 40/00* (2013.01)

(56) References Cited

U.S. PATENT DOCUMENTS

| | | | |
|---|---|---|---|
| 6,692,915 | B1 | 2/2004 | Nallur |
| 6,830,884 | B1 | 12/2004 | Hafner et al. |
| 6,921,638 | B2 | 7/2005 | Liu et al. |
| 7,462,452 | B2 | 12/2008 | Williams et al. |
| 7,553,619 | B2 | 6/2009 | Kumar et al. |
| 7,785,790 | B1 | 8/2010 | Church et al. |
| 7,807,043 | B2 | 10/2010 | Tsai et al. |
| 8,198,028 | B2 | 6/2012 | Rigatti et al. |
| 8,685,732 | B2 | 4/2014 | Font Perez et al. |
| 8,716,190 | B2 | 5/2014 | Fu et al. |
| 8,778,849 | B2 | 7/2014 | Bowen et al. |
| 9,274,077 | B2 | 3/2016 | Esfandyarpour et al. |
| 9,512,422 | B2 | 12/2016 | Barnard et al. |
| 9,624,538 | B2 | 4/2017 | Church et al. |
| 2002/0027072 | A1 | 3/2002 | Cui et al. |
| 2003/0165948 | A1 | 9/2003 | Alsmadi et al. |
| 2004/0121338 | A1 | 6/2004 | Alsmadi et al. |
| 2004/0191784 | A1 | 9/2004 | Abarzua et al. |
| 2004/0251131 | A1 | 12/2004 | Ueno et al. |
| 2006/0134657 | A1 | 6/2006 | Hodko et al. |
| 2009/0075390 | A1 | 3/2009 | Linder et al. |
| 2009/0137423 | A1 | 5/2009 | Higson |
| 2010/0032319 | A1 | 2/2010 | Okada et al. |
| 2010/0062454 | A1 | 3/2010 | Kido et al. |
| 2010/0300898 | A1 | 12/2010 | Sato et al. |
| 2011/0085227 | A1* | 4/2011 | Verschueren ......... G02F 1/1679 216/17 |
| 2011/0139636 | A1 | 6/2011 | Lai et al. |
| 2011/0201099 | A1 | 8/2011 | Anderson et al. |
| 2011/0223585 | A1 | 9/2011 | Gullberg et al. |
| 2012/0045368 | A1 | 2/2012 | Hinz et al. |
| 2012/0103836 | A1* | 5/2012 | Hori ...................... G01N 27/305 205/792 |
| 2012/0231974 | A1 | 9/2012 | Kim et al. |
| 2012/0242748 | A1* | 9/2012 | Katakis ................... B41J 2/135 347/44 |
| 2013/0098775 | A1 | 4/2013 | Pei et al. |
| 2013/0140177 | A1 | 6/2013 | Lin et al. |
| 2014/0200167 | A1 | 7/2014 | Prakash |
| 2016/0186240 | A1 | 6/2016 | Andreyev et al. |
| 2016/0316540 | A1* | 10/2016 | Aristizabal .......... H05B 33/145 |
| 2017/0022548 | A1 | 1/2017 | Öhman et al. |
| 2018/0327837 | A1 | 11/2018 | Esfandyarpour et al. |

FOREIGN PATENT DOCUMENTS

| | | |
|---|---|---|
| CN | 103895376 A | 7/2014 |
| CN | 104359962 A | 2/2015 |
| EP | 0 352 138 A2 | 1/1990 |
| RU | 2415410 C2 | 3/2011 |
| WO | 2014/076209 | 5/2014 |
| WO | 2014/076214 | 5/2014 |
| WO | 2017/096491 | 6/2017 |
| WO | 2018/122852 | 7/2018 |
| WO | 2018/122856 | 7/2018 |

OTHER PUBLICATIONS

An International Search Report and a Written Opinion both dated Apr. 12, 2018, which issued during the prosecution of Applicant's PCT/IL2017/051403.
An International Preliminary Report on Patentability dated Jul. 2, 2019, which issued during the prosecution of Applicant's PCT/IL2017/051403.
Barsky, V.E., Kolchinsky, A.M., Lysov, Y.P. et al. Molecular Biology (2002) 36:437.—Abstract.
Christian Korthage, Evelyn Fricke, Andreas Meier, Andreas Geipel, Mark Baltes, Nadine Krüger, Florian Herschel, Christoph Erbacher; Clonal rolling circle amplification for on-chip DNA cluster generation, Biology Methods and Protocols, vol. 2, Issue 1, Jan. 1, 2017.
Laux EM., Bier F.F., Hölzel R. (2018) Dielectrophoretic Stretching of DNA. In: Zuccheri G. (eds) DNA Nanotechnology. Methods in Molecular Biology, vol. 1811. Humana Press, New York, NY—Abstract.
An English Translation of an Office Action dated Jan. 29, 2021, which issued during the prosecution of Russian Patent Application No. 2019119763.
An Invitation to pay additional fees dated Nov. 13, 2019, which issued during the prosecution of Applicant's PCT/IL2019/050741.
An Office Action together with English Summary dated Jul. 26, 2022 which issued during the prosecution of Chinese Patent Application No. 201780087692.X.

* cited by examiner

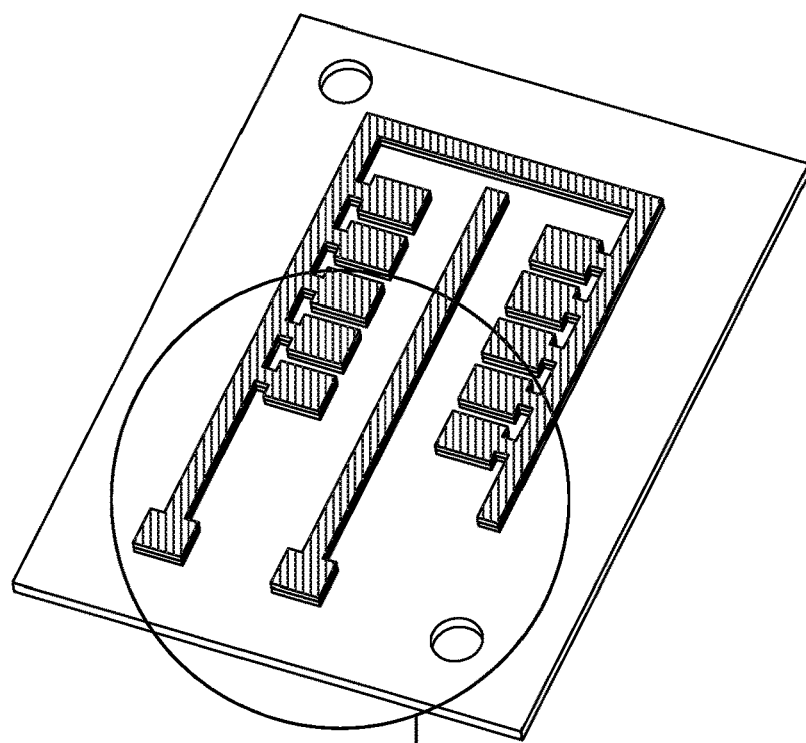
Fig. 1b
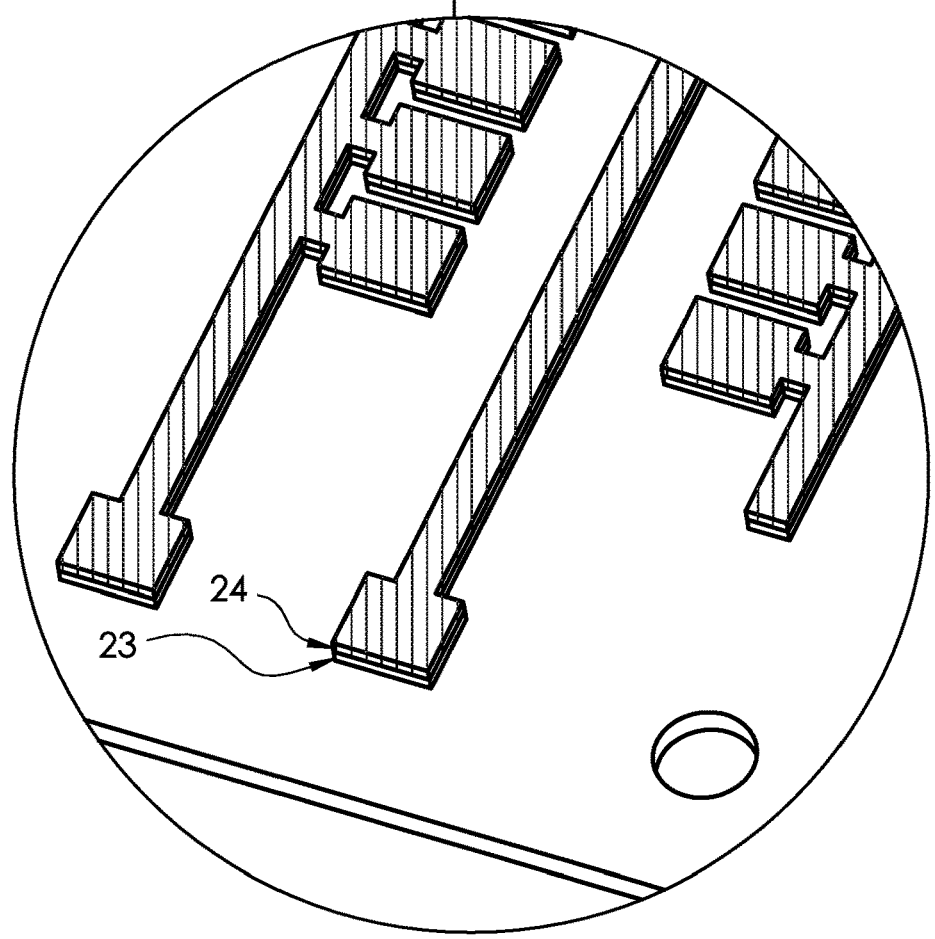

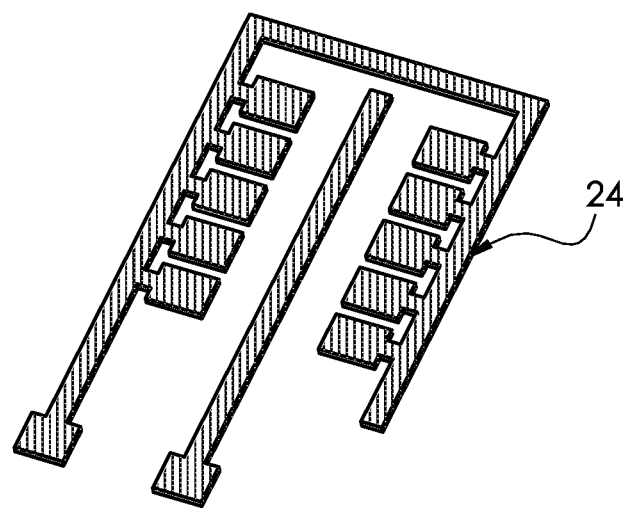
Fig. 2
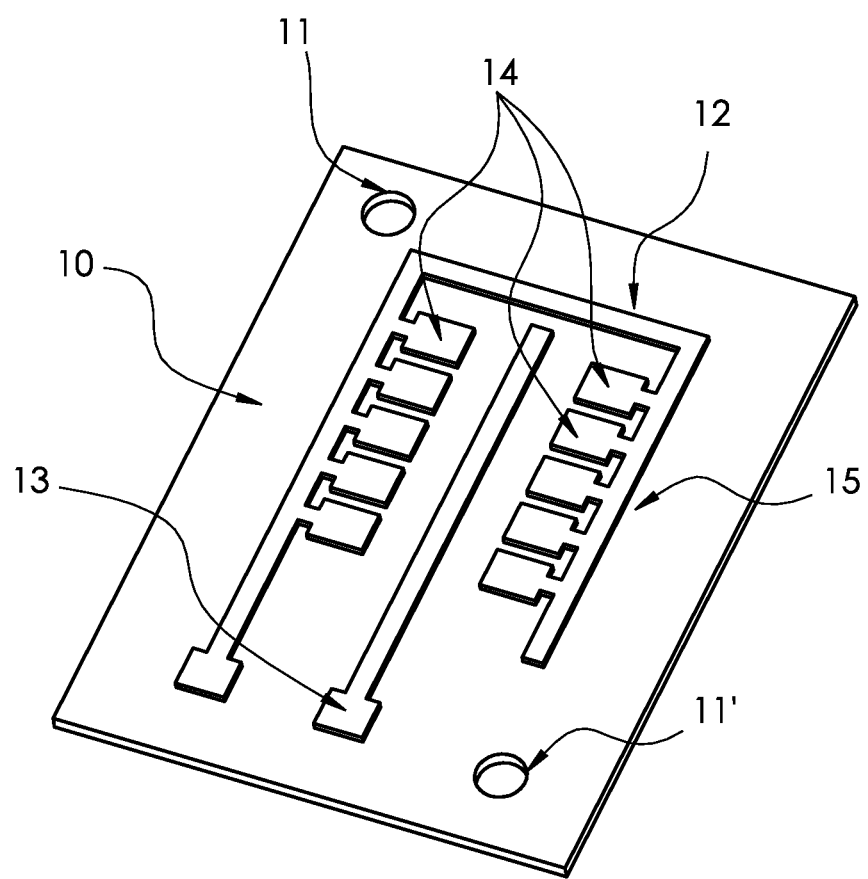

Fig. 9a (prior-art)

Fig. 9b (prior-art)

Fig. 10a (prior-art)
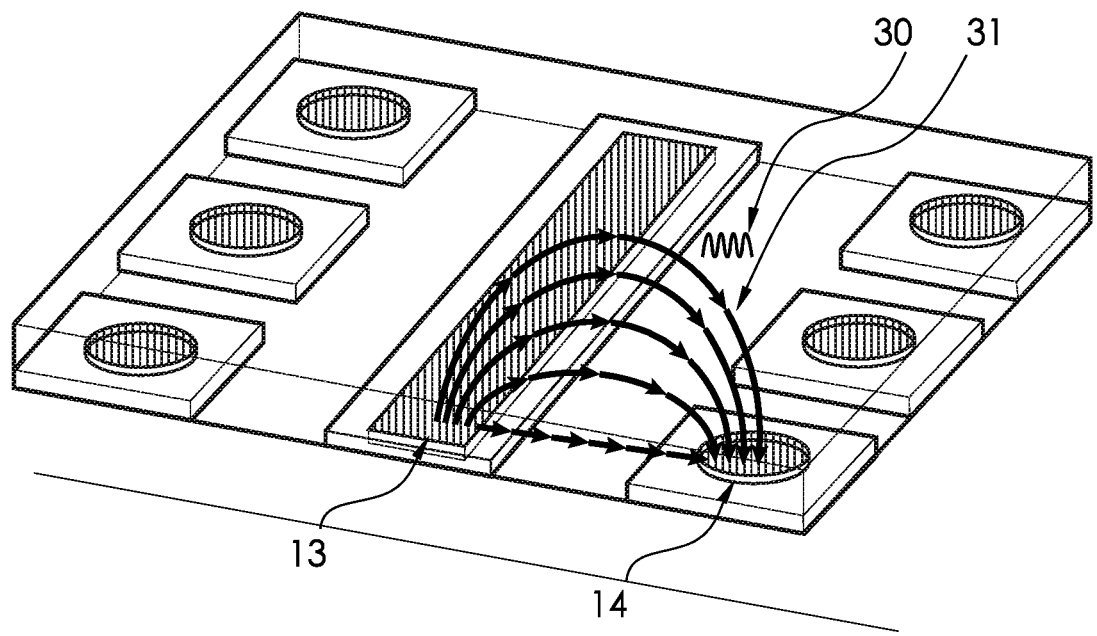
Fig. 10b
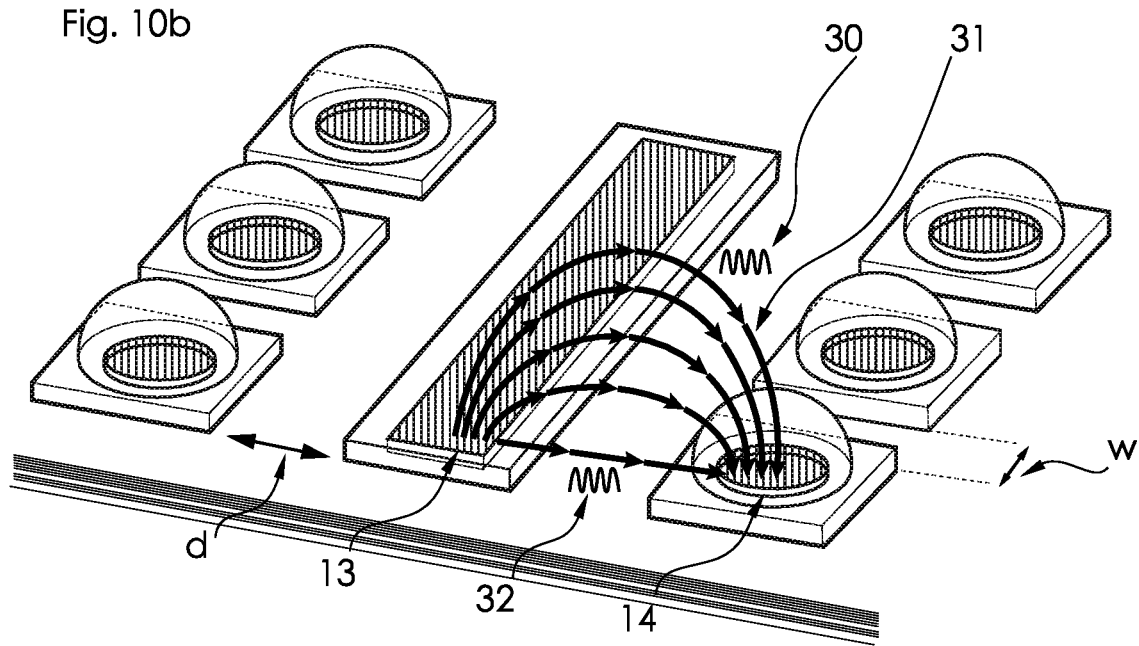

Fig. 12a (prior-art)

Fig. 12c (prior-art)

Fig. 13a (prior-art)
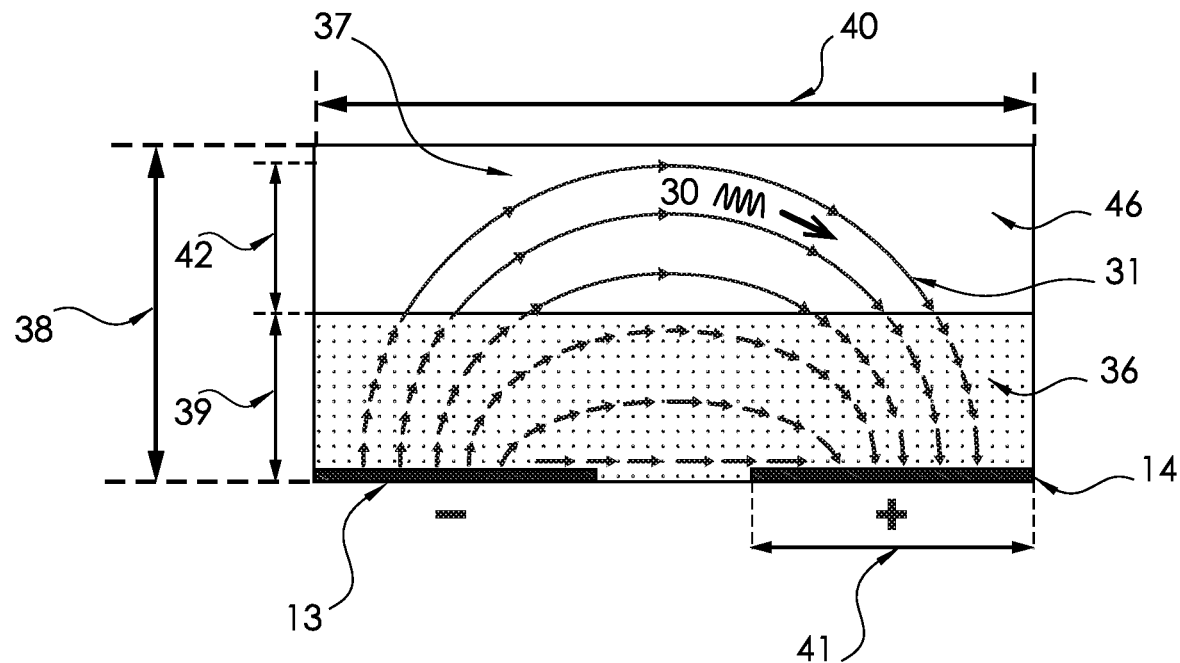
Fig. 13b
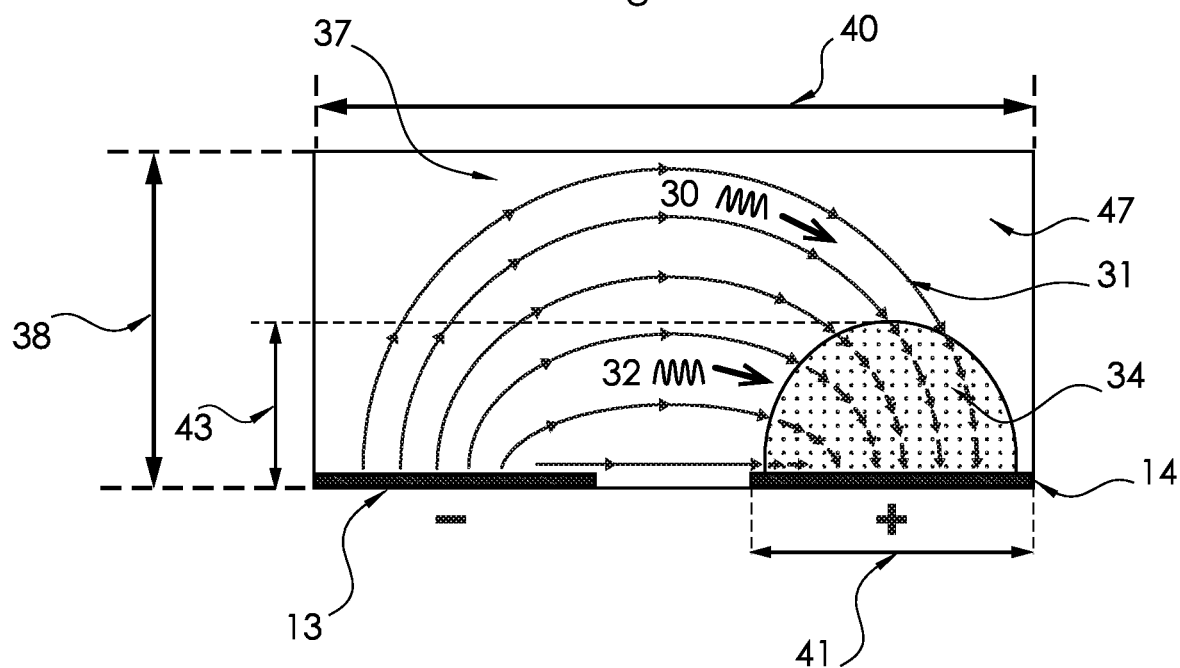

ELECTROPHORETIC CHIP FOR ELECTROPHORETIC APPLICATIONS

CROSS REFERENCE TO RELATED APPLICATIONS

This application is a National Stage of International Application No. PCT/IL2017/051403 filed Dec. 28, 2017, claiming priority based on Israel Patent Application Nos. 249856 filed Dec. 29, 2016 and 249857 filed Dec. 29, 2016.

TECHNICAL FIELD

The present invention generally relates to electrophoretic chips and methods of use, and more particularly to electrophoretic chips including carbon array electrodes and methods for electrophoretic accumulation, separation, and/or detection of analytes.

BACKGROUND ART

Electrophoresis is a method that utilizes a relatively high electric field applied between two opposing electrodes, typically disposed within a gel or in a solution to move or transport charged molecules or particles of interest. The field strength E for the field applied between equal but oppositely charged electrodes can be calculated by the following formula:

$$E = V/d$$

where d (in metre units) represents the separation between the electrodes and V (in volt units) represents the potential difference placed across the electrodes. Thus, according to the above field intensity formula, the smaller the distance between the electrodes, the stronger the electric field becomes if the potential difference is held constant.

The electric field can range typically from 5 to 20 V/cm, and up to 5 kV/cm. Direct current (DC) or alternating current (AC) fields can be applied for accumulation, separation and/or detection of the analyte. In particular, gel electrophoresis is widely used for separation, purification or analysis of biological molecules, in particular their size, or their concentration. Examples of charged entities transported and analysed by various electrophoresis methods can include nucleic acids and proteins, but also cells, and micro- and nano-particles.

Printing of electrode materials, which are based on the printed inks, onto a substrate presents a relatively low-cost method producing electrodes and controlling their properties. The electrode array devices for electrophoretic applications have not been commonly used. The printed electrodes have previously been used in many different electroanalytical devices and fluidic chips using various electrochemical methods for detection of analytes in solutions. These electrochemical methods are typically based on redox-type reactions, where the analyte molecules are oxidized or reduced at the electrode surface, and the current flowing through the electrode is measured and is proportional to the concentration of the analyte in solution. Thus, in the electrochemical techniques, where the electric current is measured as a function of the analyte concentration, the working (sensing) electrodes need to be made of materials, such as platinum or carbon inks, that are highly electroactive, meaning they are capable of promoting the oxidation or reduction of the specific analyte. This is because the electroanalytical or electrochemical applications require electrode materials that enable high currents to occur on the electrodes and have surface properties that promote a particular oxidation/reduction reaction of the analyte.

Gel electrophoresis, which is significantly different in nature from most of the electrochemical analytical methods, has been extensively used in biotechnology, molecular biology, biochemistry, physical chemistry, medicine, pharmaceutical sciences, veterinary medicine, nanotechnology, and other fields for many decades. Molecules, in particular large biomolecules, such as DNA/RNA or proteins, require application of high electric fields to be efficiently transported through the transport medium (gel or solution) and separated or concentrated within the gel matrix. Therefore, strong electric fields are needed for their transport, particularly through the gel matrix.

The electric field is applied between two electrodes, namely anode (positively charged) and cathode (negatively charged), which are placed in separate buffer reservoirs that face a gel matrix, prepared at a controlled porosity. A sample of the analyte molecules is inserted or pipetted into the gel, and the molecules are separated in time as they move through the gel matrix in accordance with their different electrophoretic mobility. The electrophoretic mobility of molecules depends not only on charge, size and shape of the molecules, but also on the physicochemical properties of the gel matrix, such as viscosity, dielectric permittivity, pH value, salts composition, and the pore size of the gel matrix. There are a large number of designs known for electrophoresis apparatus and their cartridges, including, e.g., the pre-cast gels embedded within a disposable cartridge. The cartridges are typically made based on platinum wire electrodes or carbon-based rod electrodes, which are relatively expensive.

Fanjul☐Bolado et al. (2008) in *"Electrochemical characterization of screen-printed and conventional carbon paste electrodes"*, Electrochimica Acta 53 (10), 2008, pages 3635-3642, compares the electroactivity of a conventional carbon paste electrode and non-pre-treated commercially available screen-printed carbon electrodes towards some redox couples. In this context, it should be mentioned that electroactivity of electrodes for electrophoresis differs from electroactivity of electrodes for electrochemical analysis. This is determined by inherent properties of the electrode material. In particular, metals or metallised surfaces enable an easy electron transfer between the redox or analyte molecule in solution and the metal electrode surface. In addition, for electroanalytical purposes, the electrode material must exhibit relatively high electron conductivity and transport within the material matrix itself.

Metals show high electron transport, because they have high concentration of free electrons in their conduction band. Oppositely, semiconductors may not have the high concentration of free electrons in the conduction band. Therefore, semiconductors do not normally create strong electric current, unless they are doped, or thermally or optically excited. However, since the electron transport in electrophoresis may not require too high electric currents, the semiconductor additives in the printed pastes may efficiently promote the electrophoretic processes.

Apart from the semiconductors, such as silicon and germanium, many metal oxides, such as titanium dioxide, indium oxide, iron and nickel oxides, and metal sulphides, tellurides and selenides, such as cadmium sulphide and cadmium telluride, exhibit semiconducting properties. The semiconducting materials and additives to the printed pastes prepared from these materials therefore exhibit higher resistance at the electrode/electrolyte interface. This creates higher voltages at the electrode/electrolyte interface and makes an electrophoretic process more efficient at these high voltages, since the electrophoretic transport of large molecules through a gel matrix proceeds smoothly under higher electric fields applied. The resistance of the ink-based electrode materials can then easily be modified by preparing the ink mixtures that contain more insulating and/or semiconducting additives in the ink formulation.

Hydrolysis of water at the electrode surfaces typically occurs during the process of electrophoresis. This results in intense bubbling at the electrodes which may interfere with the electric current flow, thereby preventing the separation or accumulation of the analyte and obscuring the optical signals on the electrophoretic array. It is possible to suppress the electrochemical hydrolysis of water at the electrodes and bubbling by using semiconductors or insulating materials in addition to metals. Such composite materials facilitate other electrochemical reactions than water hydrolysis. Siebert (1963) in "*Electrochemical Oxidation of Titanium Surfaces*", Journal of the Electrochemical Society, 110 (1), 1963, pages 65-72, suggested using titanium metal or additives containing titanium (which is by nature a semiconductor) for manufacturing anodes, wherein oxidation of titanium and formation of titanium dioxide at the electrode surface efficiently inhibits water hydrolysis and bubbling. The present inventors have also demonstrated, as described in U.S. Pat. No. 7,134,542, that using a buffer electrolyte with a reducing agent as an additive to the buffer, such as alpha-thioglycerol, can suppress the oxygen evolution at positive potentials.

U.S. Pat. No. 6,303,015 describes palladium or nickel composite materials containing amorphous metallic glass electrodes used as cathodes, wherein hydrogen evolution is suppressed at the surface of the electrodes, since hydrogen is instantly absorbed by the metals and forms metal hydrides. As a result, as described by Searson (1991) in "*Hydrogen Evolution and Entry in Palladium at High Current Density*", Acta Metallurgica et Materialia, 39 (11), 1991, pages 2519-2525, water hydrolysis is overcome by an electrochemical hydride formation within the metal lattice. Other types of reactions that occur at the electrode surface, that can suppress, inhibit or replace water splitting at the electrodes, may include oxidation of carbon inside the carbon inks into carbon monoxide or other oxidation products.

Use of screen-printed electrodes in the electrochemical detection is generally described in U.S. Pat. No. 6,878,255 and in J. Wang, Analytical Electrochemistry, $2^d$ Ed, Wiley, VHC, New York, 2000. EP 0352138 describes using ink structures in strip-type screen-printed electrodes and/or chips, where the surface is highly conductive and electroactive, for electrochemical detection of various analytes, predominantly glucose sensing. U.S. Pat. Nos. 7,297,248 and 8,268,604 disclose metal-containing inks that may help in embedding enzymes, such as glucose oxidase, as reaction catalysts within the electrode surface, in order to enable the electrochemical detection of glucose. U.S. Pat. No. 7,479,211 relates to methods for fabrication of printed biosensors, where the electrodes are made using laser ablation of metallic conductors on plastic non-conductive surfaces, for electrochemical detection of glucose, cholesterol, triglycerides, lactate and bilirubin. U.S. Pat. No. 8,105,477 shows the use of carbon ink-based electrodes for electrochemical detection of nucleic acids. EP 2147305 relates to using resistive carbon inks in glucose strip biosensors that show various resistances based on their resistor values and are capable of identifying the event of inserting the strip into the measuring device.

Although many electrochemical devices have been designed using the above screen-printed carbon-ink based electrodes exhibiting higher conductivity and electro-activity of the structures, electrophoretic devices that utilize the screen-printed electrodes have not been widely known. U.S. Pat. No. 8,268,018 describes the use of carbon screen-printed electrodes to control an iontophoretic delivery of drugs through the skin as a part of a portable device. U.S. Pat. No. 6,878,255 and Wang et al. (2000) in "*Capillary Electrophoresis Chips with Thick-Film Amperometric Detectors: Separation and Detection of Hydrazine Compounds*", Electroanalysis 12 (9), 2000, pages 691-694, disclose the use of thick-film electrodes, which may be fabricated using screen-printing methods, for electrophoretic applications that relate to microscale capillary electrophoresis. However, no electrophoretic devices disclosed in the prior art teach embedding electronics elements within the electrode structure and modifying the electrode composition or their layered properties to achieve current and/or voltage control for enhancement of the (die)electrophoretic processes.

In typical electrophoretic devices, the separation and accumulation process is performed through the gel using a constant current, which is applied from an external power source. A relatively high voltage of about 50-200 V is required to overcome the gel resistance. The electrodes placed in a buffer exhibit typically low overall resistance, especially when platinum electrodes are used, because of their high electroactivity. Each electrode has its own wire and contact to the power source. However, such conventional electrodes are not capable of controllably increasing their resistance in the same buffer. Increasing the resistance would allow increasing the total voltage between the working and counter electrodes for the same constant current. As a result, the molecular transport might be performed through the gel at much higher electric fields, yet at the same current compared to the conventional electrodes.

Thus, there is a long-felt need in the electrophoretic devices based on the electrodes having layered structures and geometries of the printed inks and incorporating electronics elements. Such devices may significantly enhance the electrophoretic processes and may offer a low-cost platform for fluidic chips and devices utilising various electrophoretic and dielectrophoretic processes.

SUMMARY OF INVENTION

In one aspect, the present invention provides an electrophoretic chip comprising:
(a) a non-conductive substrate designed to support elements of said electrophoretic chip;
(b) an electrode structure for conducting electric current through said electrophoretic chip, printed on said non-conductive substrate and comprising a counter electrode and at least one working electrode, each electrode comprising:
  (1) a conductive low-resistance ink layer printed on the non-conductive substrate; and
  (2) a carbon ink layer printed on top of, and fully or partially covering, said conductive low-resistance ink layer;
(c) a dielectric ink insulator layer placed on top of, and covering, said electrode structure, said dielectric ink insulator layer having at least one opening above the counter electrode and at least one opening above said at least one working electrode, thereby forming at least one addressable location; and (d) a molecule capturing matrix spotted on and covering said at least one addressable location, thereby creating at least one microgel region.

In certain embodiments, the electrophoretic chip disclosed herein comprises a single working electrode and a plurality of the openings above said single working electrode. Particular such embodiments are those wherein each one of said openings is positioned at equal distance from the counter electrode, thereby forming a plurality of addressable locations over said single working electrode.

In other embodiments, the electrophoretic chip disclosed herein comprises at least two working electrodes and one opening above each one of said working electrodes. Particular such embodiments are those wherein each one of said openings is positioned at equal distance from the counter electrode, thereby forming plurality of addressable locations. Such electrophoretic chips may be configured such that said at least two working electrodes are electrically connected to a contact line via connecting areas.

In another aspect, the present invention provides an electrophoretic device comprising an electrophoretic chip as defined hereinabove, fluid inlet and outlet, a fluid driver, and a reader.

In a further aspect, the present invention relates to a method for electrophoretic accumulation and detection of at least one analyte in a solution, comprising the steps of (i) applying said solution to an electrophoretic chip or an electrophoretic device, as defined hereinabove; (ii) applying voltage to the electrophoretic chip thereby accumulating molecules of said at least one analyte at said at least one addressable location; (iii) removing free (not bound) molecules of said at least one analyte from the solution; and (iv) detecting the presence of the accumulated molecules of said at least one analyte at said at least one addressable location.

BRIEF DESCRIPTION OF DRAWINGS

Disclosed embodiments will be understood and appreciated more fully from the following detailed description taken in conjunction with the appended drawings. The drawings included and described herein are schematic and are not limiting the scope of the disclosure. It is also noted that in the drawings, the size of some elements may be exaggerated and, therefore, not drawn to scale for illustrative purposes. The dimensions and the relative dimensions do not necessarily correspond to actual reductions to practice of the disclosure.

FIG. 1b schematically shows a close-up of the two ink layers 23 and 24 printed on the non-conductive substrate 10.

FIG. 2 schematically shows the electrophoretic chip of the present invention comprising the following elements: 10—non-conductive substrate, 11—inlet printed-through hole, 11'—outlet printed-through hole, 12—common contact line, 13—counter electrode, 14—working electrodes of the working electrode array, 15—working electrode array, 24—carbon ink layer.

FIGS. 9a-9c schematically show comparison between a prior-art gel-electrophoresis device (FIG. 9a), a prior-art electrophoretic chip having a bulk gel layer 36 (FIG. 9b) and the electrophoretic chip of the present application having a matrix of microgels 34 (FIG. 9c).

FIG. 10a schematically shows a 3D view of a prior-art electrophoretic chip with a counter electrode 13 and an array of working electrodes 14 positioned in a single plane and having bulk gel layer 36 over the electrodes. This figure illustrates electrophoretic transport of analyte molecules 30 from the counter electrode 13 to the array of the working electrodes 14 through the bulk gel layer 36 along electric field lines 31 formed once voltage is applied to the chip.

FIG. 10b schematically shows a 3D view of the electrophoretic chip of the present application with counter electrode 13 and an array of working electrodes 14 positioned in a single plane and having microgels 34 spotted over the electrodes. This figure illustrates electrophoretic transport of analyte molecules 30 and 32 from the counter electrode 13 to the array of the working electrodes 14 spotted with microgels 34 along electric field lines 31 formed once voltage is applied to the chip.

FIG. 12a schematically shows a 3D view of the working electrode 14 of the prior-art electrophoretic chip shown in FIGS. 9b and 10a, having a bulk gel 36 over the electrodes.

FIG. 12c corresponds to FIG. 12a and schematically shows a side view of the working electrode 14 of the prior-art electrophoretic chip shown in FIGS. 9b and 10a and having a bulk gel layer 36 deposited over the electrode.

FIG. 13a corresponds to FIGS. 9b, 10a, 12a and 12c, and schematically shows electrophoretic transport of the analyte molecules 30 from the counter electrode 13 to the working electrodes 14 through the bulk gel layer 36. Molecules 30 are transported along electric field lines 31 formed once voltage is applied to the chip.

FIG. 13b corresponds to FIGS. 9c, 10b, 12b and 12d, and schematically shows electrophoretic transport of the analyte molecules 30 and 32 from the counter electrode 13 to the working electrodes 14 spotted with microgels 34. These molecules are transported along electric field lines 31 formed once voltage is applied to the chip.

FIG. 18a shows the detection and recognition assay for *Leishmania major* versus other leishmanial subtypes, commonly found in several types of sand flies.

FIG. 18b shows the detection and recognition assay for *Legionella pneumoniae* as a part of the triplex assay for the community acquired pneumonia assay.

DETAILED DESCRIPTION

Figure 1A:
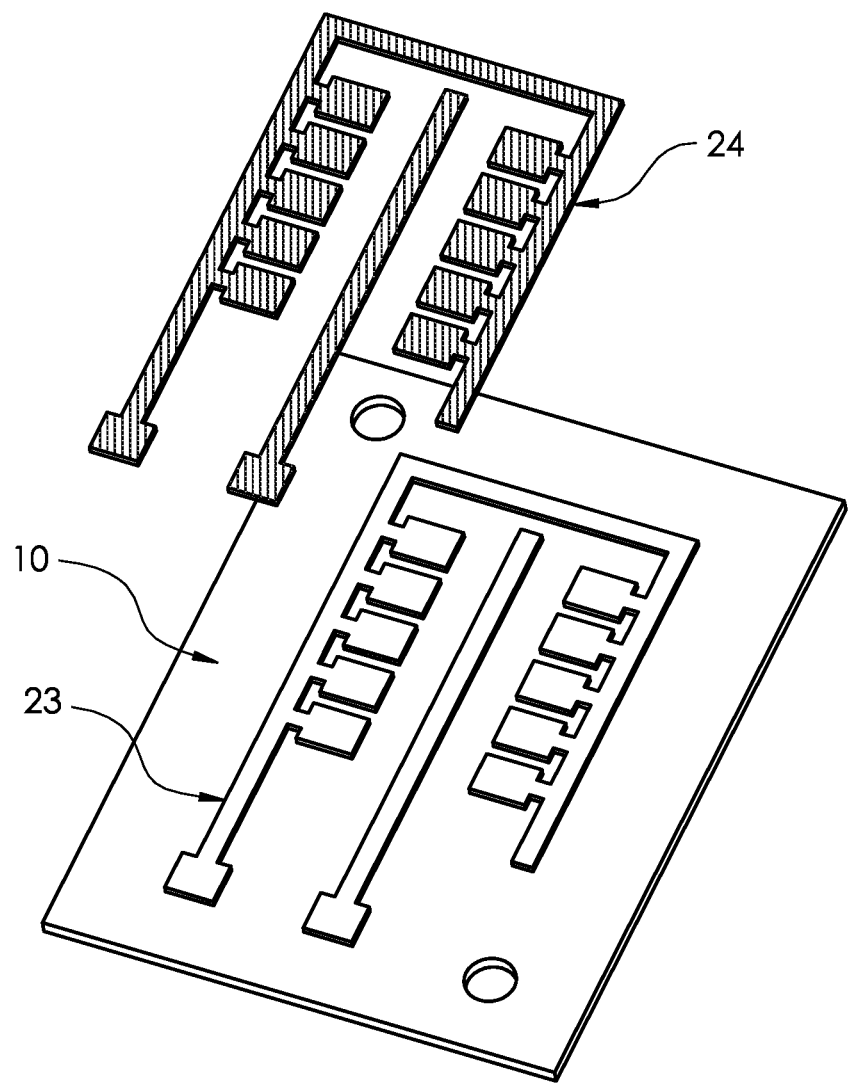
FIG. 1a shows an exploded view of the electrode structure of the electrophoretic chip of the present invention, a low-resistance ink layer 23 and carbon ink layer 24, which are printed on a non-conductive substrate 10.

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention. In the following detailed description of various embodiments, reference is made to the accompanying drawings that form a part thereof, and in which are shown by way of illustrating specific embodiments in which the invention may be practiced. It is understood that other embodiments may be utilized, and structural changes may be made without departing from the scope of the present invention.

The terminology used herein is for describing particular embodiments only and is not intended to limit the invention. The terms "comprising" and "comprises" used in the claims should not be interpreted as being restricted to the means listed thereafter; they do not exclude other elements or steps. They need to be interpreted as specifying the presence of the stated features, integers, steps and/or components as referred to, but does not preclude the presence and/or addition of one or more other features, integers, steps or components, or groups thereof. Thus, the scope of the expression "a device comprising x and z" should not be limited to devices consisting only of components x and z. Also, the scope of the expression "a method comprising the steps x and z" should not be limited to methods consisting only of these steps.

As used herein, the term "about" or "approximately" is understood as within a range of normal tolerance in the art, e.g., within two standard deviations of the mean. In one embodiment, the term "about" or "approximately" means within 10% of the recited numerical value of the number with which it is being used, preferably within 5% of the recited numerical value. For example, the term "about" or "approximately" can be immediately understood as within 10%, 9%, 8%, 7%, 6%, 5%, 4%, 3%, 2%, 1%, 0.5%, 0.1%, 0.05%, or 0.01% of the stated value. In other embodiments, the term "about" or "approximately" can mean a higher tolerance of variation depending on for instance the experimental technique used. Said variations of a specified value are understood by the skilled person and are within the context of the present invention. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges, e.g., from 1-3, from 2-4, and from 3-5, as well as 1, 2, 3, 4, 5, or 6, individually. This same principle applies to ranges reciting only one numerical value as a minimum or a maximum. Unless otherwise clear from the context, all numerical values provided herein are modified by the term "about" or "approximately". Other similar terms such as "substantially", "generally", "up to" and the like are to be construed as modifying a term or value such that it is not an absolute. Such terms will be defined by the circumstances and the terms that they modify as those terms are understood by those of skilled in the art. This includes, at very least, the degree of expected experimental error, technical error and instrumental error for a given experiment, technique or an instrument used to measure a value.

As used herein, the term "and/or" includes any combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached to", "connected to", "coupled with", "contacting" etc., another element, it can be directly on, attached to, connected to, coupled with or contacting the other element or intervening elements may also be present. In contrast, when an element is referred to as being, e.g., "directly on", "directly attached to", "directly connected to", "directly coupled" with or "directly contacting" another element, there are no intervening elements present. It will also be appreciated by those of skill in the art that references to a structure or feature that is disposed "adjacent" another feature may have portions that overlap or underlie the adjacent feature.

In one aspect, the present invention provides an electrophoretic chip comprising:
(a) a non-conductive substrate designed to support elements of said electrophoretic chip;
(b) an electrode structure for conducting electric current through said electrophoretic chip, printed on said non-conductive substrate and comprising a counter electrode and at least one working electrode, each electrode comprising:
  (1) a conductive low-resistance ink layer printed on the non-conductive substrate; and
  (2) a carbon ink layer printed on top of, and fully or partially covering, said conductive low-resistance ink layer;
(c) a dielectric ink insulator layer placed on top of, and covering, said electrode structure, said dielectric ink insulator layer having at least one opening above the counter electrode and at least one opening above said at least one working electrode, thereby forming at least one addressable location; and
(d) a molecule capturing matrix spotted on and covering said at least one addressable location, thereby creating at least one microgel region.

The "electrophoretic chip" of the present invention is an electronic circuit or a set of electronic circuits printed on a substrate and used for electrophoresis. The gel-based electrophoretic devices currently in use commonly utilise only two-electrode systems, and a single, monolithic gel for separation of molecules. In such devices, bulk gels are deposited onto working electrodes, where the analyte accumulation occurs, while the counter electrodes are not coated with the gel. In contrast, the gel used in the electrophoretic chip disclosed herein, also referred to as "a molecule capturing matrix", is spotted onto each working electrode, more specifically onto each one of the addressable locations formed above said working electrodes, wherein each spot is referred to as a "microgel" or "microgel region". In contrast to the electrophoretic chips currently known, the microgels spotted over the electrodes are not connected and do not form a monolithic block as in the gel electrophoretic devices currently known.

In certain embodiments, the electrophoretic chip of the present invention comprises a single working electrode and a plurality of openings above said single working electrode. In particular such embodiments, each one of said openings is positioned at equal distance from the counter electrode, thereby forming a plurality of addressable locations over said single working electrode.

In other embodiments, the electrophoretic chip of the present invention comprises at least two, i.e., two or more, working electrodes and one opening above each one of said working electrodes. In particular such embodiments, each one of said openings is positioned at equal distance from the counter electrode, thereby forming plurality of addressable locations. Such electrophoretic chips may be configured such that said at least two working electrodes are electrically connected to a contact line via connecting areas. In particular such embodiments, each one of the connecting areas electrically connecting said at least two working electrodes and said contact line comprises a resistor layer printed on the non-conductive substrate, between and bridging each one of said working electrodes and said contact line. In certain such embodiments, the sheet resistance of the resistor layer is in the range $0.05-1\times10^7$ $\Omega$/square/mil. In other such embodiments, the resistor layer comprises a natural resin or a synthetic polymeric additive.

Examples of synthetic polymeric additives include, without being limited to, acrylic resins, alkyd resins, cellulosic resins, rubber modified resins, ketone resins, styrene maleic anhydride resins, polyester resins, phenol formaldehyde resins, melamine formaldehyde resins, urea formaldehyde resins, hydrocarbon resins, phenolic resins, epoxy resins, fumaric resins, isocyanate-free polyurethane resins, polyvinyl butyral resins, polyamide resins, Teflon resins, and Nafion resins.

In certain embodiments, the electrophoretic chip of the present invention has a plurality of addressable locations. Such electrophoretic chips comprise either a single working electrode and a plurality of openings, optionally positioned at equal distance from the counter electrode, above said single working electrode; or at least two working electrodes and one opening above each one of said working electrodes, wherein each one of the openings is optionally positioned at equal distance from the counter electrode, according to any one of the embodiments defined above. In particular such embodiments, the plurality of addressable locations are positioned at equal distance from the counter electrode, and each one of the addressable locations formed, upon applying voltage to the electrophoretic chip, thus receives approximately equal and uniform electric current.

As will be discussed in detail below, the phrase "equal and uniform electric current" as used herein means that each working electrode at each addressable location receives approximately equal electric current with the same current density, which is uniformly distributed over the surface of each electrode.

In certain embodiments, the electrophoretic chip of the present invention has a plurality of addressable locations, which upon applying voltage to the electrophoretic chip, receive approximately equal and uniform electric current, and said matrix creates at least two microgel regions such that the adjacent microgel regions are not in direct contact with each other.

In some embodiments, the present invention provides an electrophoretic chip as defined in any one of the embodiments above, wherein said matrix is capable of capturing or accumulating molecules at said addressable locations. In other embodiments, the invention provides an electrophoretic chip as defined in any one of the embodiments above, wherein said at least one microgel region, upon applying voltage to said electrophoretic chip, is capable of promoting an electrophoretic transport of molecules. In certain particular such embodiments, said matrix comprises a porous polymeric structure, film forming lattice, proteinaceous mixture such as photo-formable proteinaceous mixture, semipermeable solid film, or gas permeable membrane functionalised with chemical functional groups capable of forming an attachment layer. In more particular such embodiments, said matrix further comprises at least one separate layer.

In some embodiments, the present invention provides an electrophoretic chip as defined in any one of the embodiments above, further comprising capture molecules attached to or embedded within said matrix, or attached to the carbon ink layer of said at least one working electrode at the addressable location, said capture molecules being capable of binding an analyte, i.e., a target molecule.

In certain embodiments, the present invention provides an electrophoretic chip according to any one of the embodiments defined above, wherein said matrix further comprises at least one separate layer.

In certain particular such embodiments, said separate layer is an attachment layer for attaching capture molecules capable of binding a target molecule, e.g., an attachment layer comprising functional groups or chemical moieties for direct binding of said target molecule or for binding said capture molecules, and thus indirectly binding said target molecule. Particular such attachment layers may contain streptavidin chemical moiety, wherein the capture molecules are biotinylated molecules.

In other particular such embodiments, said separate layer comprises a supramolecular polymer, which is a polymer whose monomeric units hold together via highly directional and reversible non-covalent interactions, such as hydrogen bonding, $\pi$-$\pi$ interaction, metal coordination, and host-guest interaction. Examples of supramolecular polymers include, without limiting, bivalent poly(isobutylene)s (PIBs) with barbituric acid functionalized at head and tail, chain-folding polyimide and pyrenyl-end-capped chains, supramolecular cyclodextrin-based polymers, rotaxanes, ureido-pyrimidinone quadruple complex, ferrocene-$\beta$-cyclodextrin-based complex, metallo-supramolecular amphiphilic block copolymers, and pH-control self-healing supramolecular polymers containing coordination complexes, such as mono-, bis- and triscatehchol-$Fe^{3+}$. In certain specific such embodiments, the supramolecular polymer is calixarene.

In still other particular such embodiments, said separate layer is a permeation layer capable of binding a target molecule. Such a permeation layer may comprise sites for binding capture molecules capable of binding said target molecule, thereby acting as an accumulation layer for said target molecule.

The term "capture molecule" as used herein refers to a molecule capable of capturing a target molecule or analyte by either covalent or non-covalent binding. According to the present invention, particular capture molecules are those that are specific to a particular molecular recognition group of said target molecule.

As used herein, the terms "analyte", "analyte molecule", "target" and "target molecule" are completely equivalent and interchangeable, and define a molecule or compound whose (bio)chemical structure being identified and/or whose (bio)chemical, (bio)physical and/or spectral properties being measured. Examples of target molecules include, without limiting, charged macromolecules and micro- and nano-entities, such as proteins, enzymes, ssDNA, ssRNA, dsDNA, dsRNA, receptors, aptamers, antibodies, antigens, different cells, human, or animal genomic DNA or DNA/RNA collected from microorganisms including bacteria and viruses, micelles, vesicles, exosomes, molecular assemblies, such as DNA nanoballs, and nanomaterials, such as carbon nanotubes or nanoparticles.

In certain embodiments, the present invention provides an electrophoretic chip according to any one of the embodiments defined above, wherein the diameter of said at least one microgel region is in the range of 1 nm to 1 cm, depending on the electrode dimensions and electrophoretic application method, and the height of said at least one microgel region is in the range of 1 nm to 1 mm. The diameter of the microgel region is preferably in the range of 50-500 microns, and the microgel height is preferably in the range of 5-500 microns.

In certain embodiments, the present invention provides an electrophoretic chip according to any one of the embodiments defined above, wherein said carbon ink layer has overpotential for hydrogen evolution less than −0.07 V. In particular such embodiments, said carbon ink layer further comprises particles of a metal such as zinc, iron, nickel, palladium, lead or mercury.

In certain embodiments, the present invention provides an electrophoretic chip according to any one of the embodiments defined above, wherein said carbon ink layer has overpotential for oxygen evolution more than +0.77 V. In particular such embodiments, said carbon ink layer further comprises particles of a metal such as titanium, palladium, or gold, an oxide of said metal, or a combination thereof.

In certain embodiments, the present invention provides an electrophoretic chip according to any one of the embodiments defined above, wherein said at least one opening above the counter electrode forms an addressable location over the counter electrode.

An electrophoretic chip according to any one of the embodiments defined above may further comprise a high-conductivity ink heater layer printed on the bottom side of the non-conductive substrate, e.g., wherein said non-conductive substrate comprises holes through which said high-conductivity ink heater layer extends to the top of the non-conductive substrate; or wherein said high-conductivity ink heater layer is not in contact with the electrode structure and separated from it by the non-conductive substrate. Alternatively, said electrophoretic chip may further comprise a high-conductivity ink heater layer printed on the top of the non-conductive substrate and is not in contact with the electrode structure.

In certain embodiments, the present invention provides an electrophoretic chip according to any one of the embodiments defined above, wherein said conductive low-resistance ink layer is a silver ink layer.

In certain embodiments, the present invention provides an electrophoretic chip according to any one of the embodiments defined above, further comprising a thick insulating layer of dielectric or bonded perforated substrate placed on top of said electrophoretic chip, and a cover for covering said dielectric or bonded perforated substrate, wherein said dielectric or bonded perforated substrate comprises a functional fluidic chamber or channel.

In another aspect, the present invention provides an electrophoretic device comprising an electrophoretic chip as defined in any one of the embodiments above, fluid inlet and outlet, a fluid driver, and a reader.

In a further aspect, the present invention relates to a method for electrophoretic accumulation and detection of at least one analyte in a solution, comprising the steps of (i) applying said solution to either an electrophoretic chip as defined in any one of the embodiments described above or an electrophoretic device as defined above; (ii) applying voltage to the electrophoretic chip thereby accumulating molecules of said at least one analyte at said at least one addressable location; (iii) removing free (not bound) molecules of said at least one analyte from the solution; and (iv) detecting the presence of the accumulated molecules of said at least one analyte at said at least one addressable location.

In certain embodiments, the method of the present invention further comprises the step of heating the solution using high-conductivity ink heater layer of the electrophoretic chip. The heating of the solution may be conducted prior to, after, or simultaneously with any one of the method steps.

In certain embodiments, the voltage applied to the electrophoretic chip in step (ii) of the method is in the range of 2-3000 V. In particular embodiment, the applied voltage is in the range of 5-500 V, preferably in the range of 5-50 V.

In certain embodiments, the step of removing the free analyte molecules from the solution (step (iii)) is conducted by applying washing buffers having different salt content, applying reverse polarity to the electrophoretic device, or heating the solution.

In certain embodiments, the step of detecting the binding of the analyte (step (iv)) is performed by optical, electrochemical, or radio-isotope methods.

In certain embodiments, voltage is applied to the electrophoretic chip in any one of the method steps, thereby reducing non-specific binding of the analyte molecules or promoting said method steps. In some particular such embodiments, the voltage is applied in a repetitive regime, with a polarity reversal, or in a DC or AC mode with various durations. In other particular such embodiments, the voltage is applied using a regime of superimposed AC over DC including square wave, sinusoidal, or triangular waveforms.

FIGS. 1a and 1b show an exploded and a close-up view of the electrode structure of an electrophoretic chip of the present invention. The electrode structure comprises a conductive low-resistance ink layer 23 and a carbon ink layer 24, wherein the conductive low-resistance ink layer 23 is printed directly on a non-conductive substrate 10 of the chip, and the carbon ink layer 24 is printed on top of the conductive low-resistance ink layer 23, thereby creating the final electrode structure. The carbon ink layer 24 defines the resistance of the electrode structure, thereby defining the voltage and electric field applied in the (di)electrophoretic process.

As schematically shown in FIG. 2, the exemplary electrode structure of the electrophoretic chip of the present invention comprises an array 15 of the working electrodes 14, a common contact line 12 connecting all working electrodes 14 in one array 15, and a counter electrode 13. The substrate 10 has an inlet hole 11 and an outlet hole 11' for liquid solutions to enter and exit the chip, as will be detailed below. The electrode configuration shown in FIG. 2 provides a significant enhancement and control of the electrophoretic transport. This is achieved through a symmetrical geometrical arrangement of the electrodes in the array, thereby yielding an equal and uniform electric current at each one of the working electrodes.

The electrophoretic chip of the present invention addresses several limitations, and aimed at overcoming several problems, characterizing the electrophoretic chips currently known, as will be discussed below.

The first problem solved by the present invention is how to achieve equal current at each working electrode in the array used in electrophoretic applications, and how to ensure uniform distribution of this current over the surface of each working electrode in the array. The term "equal" relates to the electric current measured in amperes, and defines a steady current having an equal quantity of electric charge flowing to each working electrode per unit of time. The term "uniform" relates to the current distribution over a given electrode surface. Uniform current distribution appears to be one of the indicators of the electrode quality. Uniform current distribution over the surface of the working electrodes is determined by the shape and dimensions of the electrodes, and by the material of the electrodes. Uniform current distribution does not change during discharge, and significantly simplifies the measurements. As mentioned above, the term "equal and uniform electric current" as used herein means that each working electrode at each addressable location receives approximately equal electric current with the same current density, which is uniformly distributed over the electrode surface. The equal current received at each one of the working electrodes, and the uniform distribution of said current on the surface of each one of said electrodes, enables in fact a non-controllable operation of the chip.

Due to the presence of the conductive low-resistance ink layer, and minimal voltage drop in the circuit, the electrons are brought almost equally to each working electrode of the electrophoretic chip of the invention, and as a result, the electric current applied at each working electrode is approximately equal. In order to achieve equal current at each working electrode, these electrodes should be spatially symmetrically positioned with respect to the counter electrode, and their addressable locations should be spaced equally with respect to the counter electrode. In addition, and in order to achieve a uniform distribution of the current, the electrodes should be made from the same material and have the same shape and dimensions, such as spatial geometry and thickness. Equal current is also determined by the resistance of the electrolyte solution between the working and counter electrodes.

The configuration of the electrode array described above does not need a separate contact to each working electrode of the array, and all working electrodes can be connected using only a single contact line. Thus, the relatively low resistance and high conductivity pattern of the working electrodes array in the electrophoretic chip of the present invention results in an equal and uniform current flow to each working electrode in the array. As mentioned above, this implies that the voltage drop along the entire contact line in the conductive low-resistance ink layer is very low. That results in no significant differences in electric current passing to each electrode through the contact line in accordance with Ohm's law under the same resistance.

The geometrical design of the electrode structure ensures a uniform electric field distribution between the counter electrode and each one of the working electrodes exposed to the counter electrode in a same geometric relationship. This geometrical design will enable establishing of a uniform field in the solution, horizontally between and above the working and counter electrodes, also known as a uniform "throwing power".

FIGS. 1a, 1b and 2 show a schematic arrangement wherein the whole working electrode array and the counter electrode are in the same plane, while in conventional arrangements, the working electrodes face directly the counter electrodes with their largest surface area. The geometry or the spatial arrangement of the electrodes demonstrated in these figures is exemplary and should not be contemplated to be limiting. Those skilled in the art may arrive at geometric configurations other than planar, but still yielding the uniform "throwing power" between the working and counter electrodes. For example, the geometric or spatial arrangement of the electrodes may be rectangular, triangular, circular, spiral, intercoiled, fractal etc. In a particular embodiment, the electrodes have a planar geometry. Since all the working electrodes have the same geometry, a uniform current distribution is achieved. To conduct approximately the same electric current, all the working electrodes in the array are positioned symmetrically, at the same distance, defined as an "electrode gap", from the counter electrode.

The second problem solved by the present invention is how to provide efficient electrophoretic transport at the surface of the electrodes. As shown herein, this is solved by creating a layered structure of the electrodes (printing the carbon ink layer on the conductive low-resistance ink layer) designed to exhibit a higher resistance at the surface exposed to electrolyte solution. In conventional electrophoretic chips, the electrode surfaces are highly conductive and do not exhibit high electric resistance. Therefore, such chips do not create voltages higher than those expected from electrochemical reactions occurring at their surface. In contrast, the layered-structured electrophoretic chip of the present invention is capable of electrophoretic accumulation and/or separation of analytes uniformly at each electrode, but under higher electric fields, and thereby enables a more efficient electrophoretic process.

In addition, the electrophoretic chip of the present invention is made using printing of inks of different resistivities, and in such a manner that the layered ink printing assures equal current distribution to each electrode in the array, as well as enhancement of the applied electric field at each electrode to enhance and accelerate the electrophoretic process.

Figure 3A:
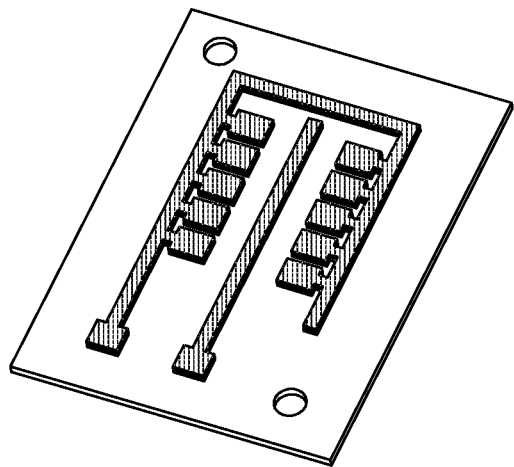
FIGS. 3a-3c schematically show the electrophoretic chip of the present invention comprising the following additional elements: 16—a dielectric ink insulator layer, 17—openings over the working electrodes forming addressable locations 19 over the working electrodes, 18—one large opening aligned with the counter electrode and leaving a portion of the counter electrode exposed to solution.
Figure 3B:
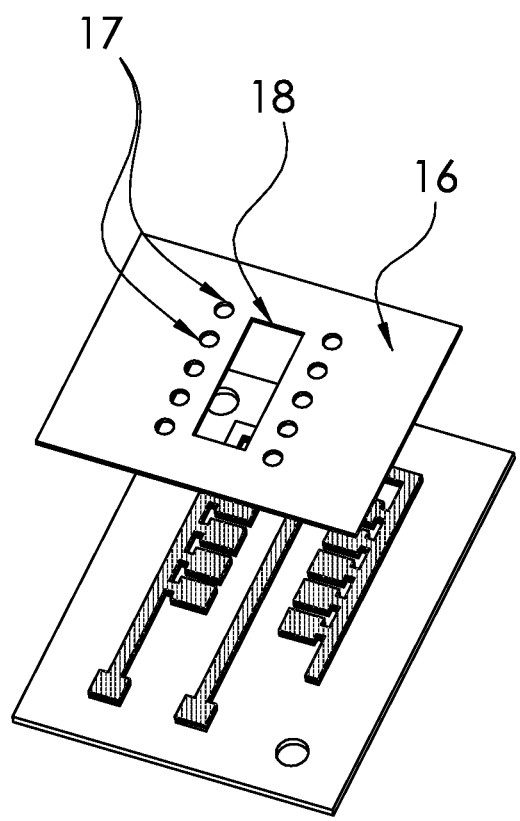
Figure 3C:
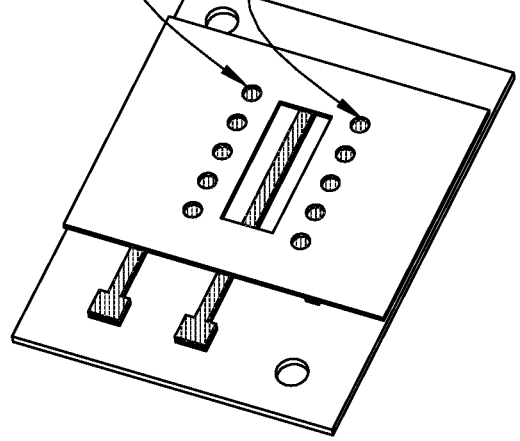

FIGS. 3a-3c schematically show an electrophoretic chip of the present invention, which further comprises a dielectric ink insulator layer 16. After the electrode structure comprising the low-resistance ink layer and the carbon ink layer is printed on the non-conductive substrate, the dielectric ink insulator layer 16 is printed on the same substrate overlaying the electrode structure such that it isolates most of the electrode structure surface from solution. The dielectric ink insulator layer 16 has several openings 17, each aligned with an individual working electrode of the working electrode array, and one relatively large opening 18 aligned with the counter electrode, thereby creating addressable locations 19 at which each of the working electrodes and a portion of the counter electrode are exposed to the solution. Thus, the "addressable locations" are defined by specific openings in the dielectric insulator layer over the electrode surface, in which the electrodes or a portion thereof are exposed to the solution. While the working electrodes are addressable through the addressable locations 19, in which they become exposed to a tested solution, the common counter electrode (or at least a portion thereof) is addressable through the opening 18.

The conductive low-resistance ink layer is designed to transfer electric current from the external power source throughout the entire electrode structure of the electrophoretic chip toward the openings 17 in the dielectric layer 16, which form the addressable locations 19. There, the current flows vertically upwards into and through the carbon ink layer, which has higher resistance than the conductive ink layer, and is designed to generate higher voltages at the electrode surface exposed to the tested solution at the addressable locations 19. This allows the current to reach all the addressable locations 19 almost simultaneously (in comparison to a situation wherein a single carbon-based ink layer is used), to make contact either directly or through gel with the solution, and to promote the electrophoretic processes in the medium, and further limits voltage drop along the pathway. Therefore, the current brought through the conductive low-resistance ink layer to each addressable location is approximately equal (since the voltage drop along this layer is minimal).

When the electric current received at each one of the working electrodes per unit of time is controlled, i.e., established, and made constant using a certain geometry, shape, and material of the electrodes, as in the electrophoretic chip disclosed herein, the electrophoretic transport becomes directly proportional to this current, thereby approximating the Faraday's law that is valid in many electrochemical and electroanalytical applications. The Faraday's law explains the quantitative transport of molecules and other charged species under an applied electric field, and postulates that the electric current is proportional to the amount of charged species transported. Since during electrophoresis, larger molecules or charged entities, e.g., micro- and nano-particles, are transported by the electric current simultaneously with the ions in the solution, their transport is defined by their electrophoretic mobility and may be impeded by the gel matrix. In solutions, transport of the larger molecules is much slower than the ionic transport and requires significantly higher electric fields for efficient electrophoresis.

The non-conductive substrate 10 may be made from various materials based on single or multiple components including plastic, rubber, silicon with a nonconductive layer of silicon dioxide, glass, ceramics, thermosetting resins, thermoplastic resins, or any planar nonconductive substrate suitable for mass production and dimensional control of overlaid structures. Suitable thermoplastic resins may include acetal resins, acrylic resins, such as methyl acrylate, cellulosic resins, such as ethyl cellulose, cellulose acetate, cellulose propionate, cellulose acetate butyrate, cellulose nitrate, chlorinated polyethers; nylon, polyethylene, polypropylene, polystyrene; styrene blends, such as acrylonitrile styrene co-polymers and acrylonitrile-butadiene-styrene co-polymers, polychlorotrifluoroethylene, polycarbonates, and vinyl polymers and co-polymers, such as vinyl acetate, vinyl alcohol, vinyl butyral, vinyl chloride, vinyl chloride-acetate co-polymer, vinylidene chloride and vinyl formal. Suitable thermosetting resins include alkyl phthalate, furane, melamine-formaldehyde, polyacrylic esters, phenol formaldehyde and phenol-furfural co-polymer, alone or compounded with butadiene acrylonitrile co-polymer or acrylonitrile-butadiene-styrene co-polymers, silicones, urea formaldehydes, epoxy resins, polyimides, alkyl resins, glyceryl phthalates, and polyesters.

The electrophoretic chip of the present invention may be "screen-printed", wherein printing ink is applied directly to the surface of the substrate (the screen) using a stencil, which defines a final pattern of the electronic circuit to be printed. This pattern is lithographically transferred to the screen such that the non-printing areas are blocked off and the screen serves as a stencil. The stencil pre-defines the areas made impermeable to the ink by blocking the screen. The ink is wiped across the screen to pass through the unblocked areas and reach the substrate. For each electronic circuit to be printed, a separate stencil is prepared, and the process is repeated. Alternatively, the electrophoretic chip may be 3D printed, printed with a jet ink, or printed using any other suitable printing technique.

The electrophoretic chip of the present invention may further comprise an optional reference electrode. Such an electrode may be useful when said electrophoretic chip is also used as an electroanalytical device. In that case, the layered ink electrode structure may combine the electrophoretic and electroactive electroanalytical features of the electrodes. In case the electrophoretic chip is connected to another chamber with another electrophoretic chip or an array thereof, the former will serve as a sensing chip, which will have inks promoting the electroanalytical applications or the electrochemical sensing. Reference electrodes are commonly used in most of the electrochemical techniques utilized to detect an analyte at the electrode surface. Thus, the reference electrode may be built as an integral part of the electrophoretic chip, e.g., using inks containing reference electrode materials such as silver/silver chloride-containing inks, or may be placed in an electrophoretic device comprising the electrophoretic chip of the invention and connected therewith.

The conductive low-resistance ink layer 23 may be made from inks comprising metal elements that exhibit low resistivity, such as silver, copper, gold, aluminium, nickel, brass, iron, tin, platinum and lead. The high-resistance carbon ink layer 24 is actually made from carbon ink paste which may further comprise additives, such as insulating fillers (e.g., Teflon-like particles or polymeric particles) that notably reduce conductivity of the carbon ink layer, semiconducting titanium oxide particles or similar, metal particles with high overpotentials for hydrogen evolution and oxygen evolution, and other relating materials that are capable of minimising oxygen/hydrogen evolution. Materials showing high overpotentials for oxygen and/or hydrogen evolution will minimise water electrolysis at the electrodes in solution, thereby minimising water bubbling. Alternatively, materials capable of inducing electrochemical reactions other than water electrolysis may be used in the carbon ink layer, such as, but not limited to, titanium dioxide used for anodes, or palladium hydrides used for cathodes.

In a specific embodiment, the carbon ink layer consists essentially of carbon and metal particles with high overpotentials for hydrogen evolution and oxygen evolution. Thus, the materials used for the preparation of ink formulations for electrophoretic applications are selected from: (i) catalytically poor metals or oxides (mixed metals or oxides thereof, a combination of oxides, or hydroxides, such as nickel oxide/hydroxide or similar) that suppress oxygen/hydrogen evolution during water electrolysis; (ii) metals capable of scavenging/absorbing gases (e.g., palladium and nickel for hydrogen); (iii) semiconducting metals or metal particles exhibiting semiconducting properties, that would require high voltages for initiation of water electrolysis; or (iv) materials that promote reactions other than water hydrolysis.

The term "overpotential" as used throughout the description refers to activation overpotential, reaction overpotential or concentration overpotential, including bubbling overpotential. It should be noted that the term "non-conductive" should not be necessarily interpreted as high overpotential for oxygen and hydrogen evolution. The application aims at minimising this evolution during the accumulation of desired analyte species from aqueous solutions. Whenever aqueous solution is electrolysed, oxygen and hydrogen bubbling occur when exceeding the electrode's materials' overpotentials. Metals such as palladium and nickel, as well as metal glasses such as combinations of zirconium, copper, aluminium and nickel-based alloys, adsorb and do not evolve large amounts of hydrogen, and are therefore capable of modifying or minimising hydrogen evolution.

Alternatively, metals capable of initiating reactions other than oxygen evolution, e.g., titanium that is capable of forming a thick titanium oxide (semiconductor) layer on the titanium metal surface when high positive voltages are applied, may be used in the ink formulations. In other words, mixing titanium in the carbon ink may provide additional control and minimisation of oxygen or hydrogen evolution during electrophoretic accumulation or other (di)electrophoretic applications. Thus, in a particular embodiment, the carbon ink layer comprises carbon and metal selected from mercury, platinum, palladium, nickel or titanium.

Figure 4:
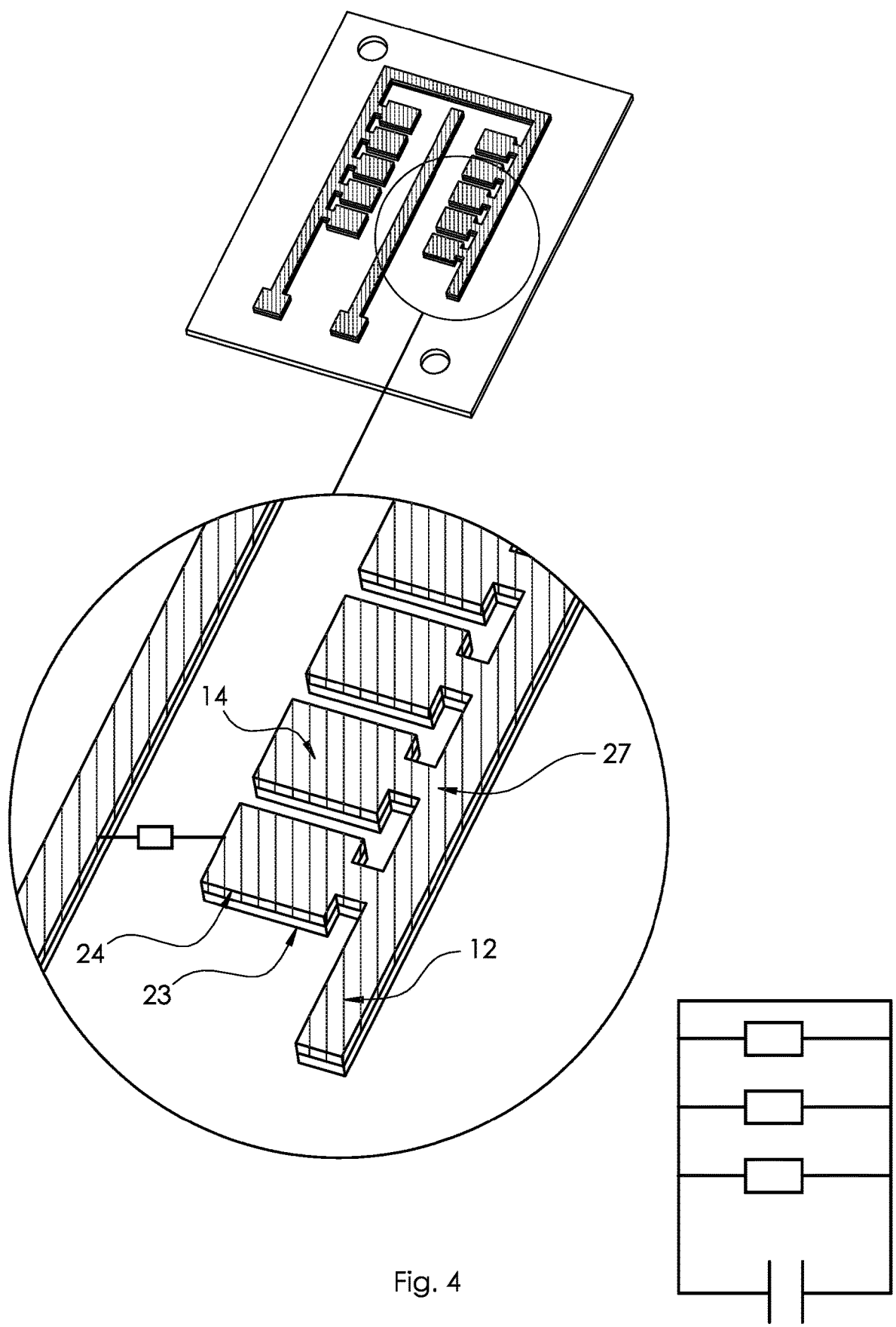
FIG. 4 schematically shows a close-up of the working electrode array of the electrophoretic chip of the present application. The working electrode array consists of individual working electrodes 14 and common contact line 12 connecting all working electrodes 14 in one array. Area 27, where an individual working electrode 14 is connected to contact line 12 is defined as a connecting area.

FIG. 4 shows a close-up of a working electrode array of an electrophoretic chip of the present invention. The working electrode array comprises individual working electrodes 14 and a common contact line 12 connecting all the working electrodes into one array. An individual working electrode 14 is defined as a "working area", while an area where an individual working electrode is connected to the contact line 12 is defined as a "connecting area" 27 for each specific working electrode 14. Thus, the conductive low-resistance ink layer 23 of the working electrode array is printed in a predetermined pattern forming at least one working area and at least one connecting area 27.

Figure 5:
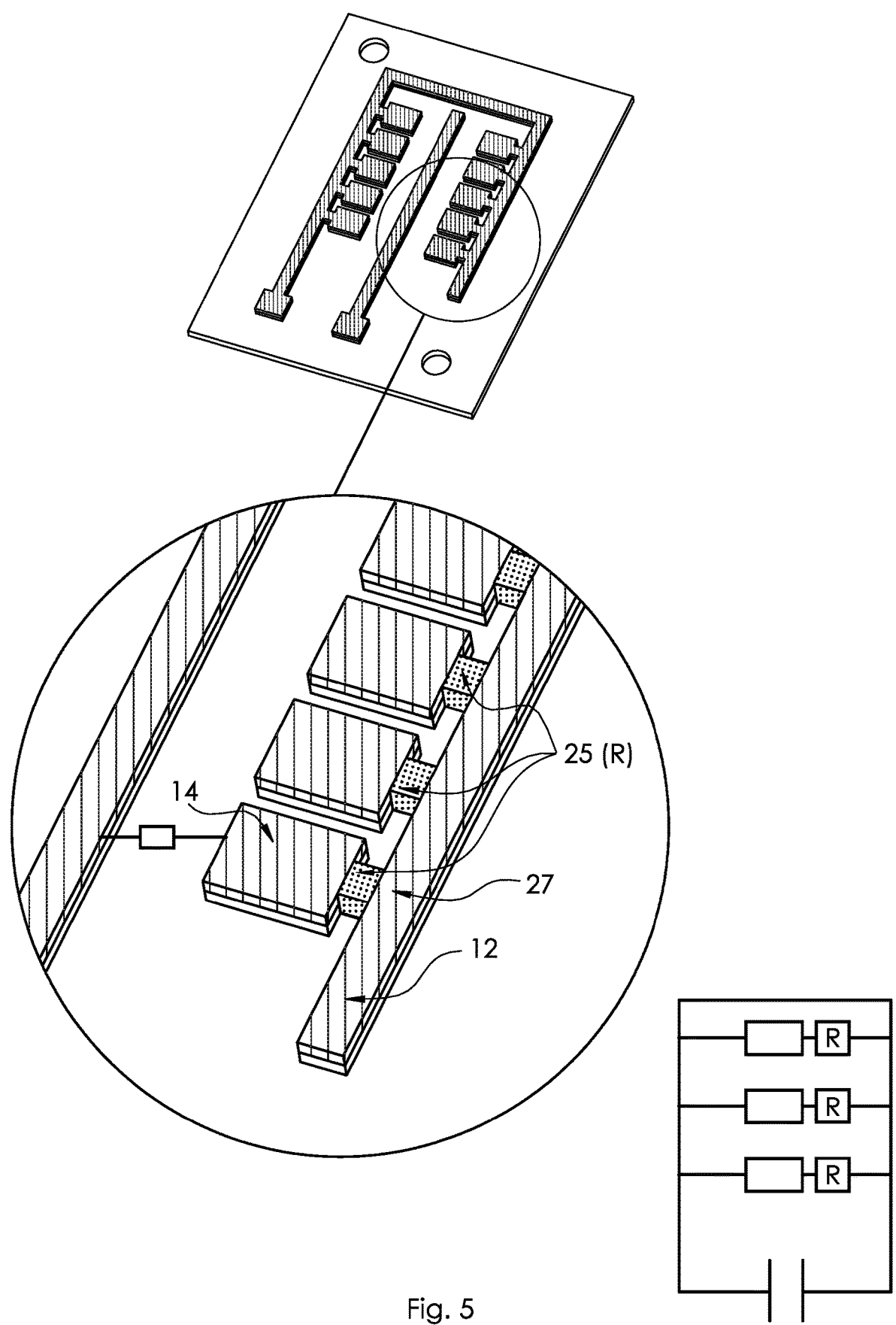
FIG. 5 schematically shows a close-up of a configuration of the electrophoretic chip of the present application comprising a resistor (R) layer 25 that is printed between each individual working electrode 14 and the common contact line 12 in the working electrode array.

In certain embodiments, each individual working electrode in the working electrode array comprises a high-resistance ink layer, such as a carbon ink layer, in between the working area and the connecting area. This layer has a resistance higher than that of the carbon ink layer, and actually acts as an electrical resistor. Therefore, this high-resistance ink layer is defined herein as a "resistor layer". FIG. 5 shows a close-up of such a configuration of the electrophoretic chip of the present invention comprising a resistor carbon ink layer (or "resistor layer") 25 printed between each individual working electrode (working area) 14 and its connecting area 27 in the working electrode array. The resistor layer 25 is printed on the substrate 10, acts as an embedded resistor of a known or desirable value, and significantly increases voltage on the electrophoretic chip, while maintaining constant current at the addressable locations 19. In a further embodiment, the conductive low-resistance ink layer 23 of the working electrode 14 is printed in a predetermined pattern forming at least one working area and at least one connecting area 27, and a resistor layer 25 is bridging each one of the working electrodes 14 with the connecting area 27.

In a particular embodiment, the resistor layer 25 has sheet resistivity that is up to 10 times higher than that of the carbon ink layer 24. As mentioned above, the sheet resistance of the resistor layer 25 may be, e.g., in the range of $0.05\text{-}1\times10^7$ Ω/square/mil, more specifically in the range of 50-500 Ω/square/mil. In some embodiments, due to the use of a resistor layer, the voltage that can be applied to the electrophoretic chip may be 2-500 V. Applying such relatively high voltage on the electrophoretic chip of the present invention allows faster transport, accumulation at the addressable locations, and better separation of analytes.

The resistor layer 25 can be prepared from ink exhibiting high sheet resistance, such as DuPont type carbon inks, e.g., DuPont 5067 and DuPont BQ221, or de novo mixed inks that exhibit even higher resistivity. The resistance of such carbon inks would depend also on the geometry of the electrodes. Thus, increasing their length, (e.g., up to several millimetres, depending on the practical geometry of the electrodes), or increasing their thickness, (e.g., in the range of 0.1-0.5 mm) would provide additional adjustment of the resistor values.

The electrophoretic chip of the present invention may further comprise a thick insulating layer of dielectric or bonded perforated substrate placed on top of said electrophoretic chip, and a cover for covering said dielectric or bonded perforated substrate, wherein said dielectric or bonded perforated substrate comprises a functional fluidic chamber or channel.

Figure 6A:
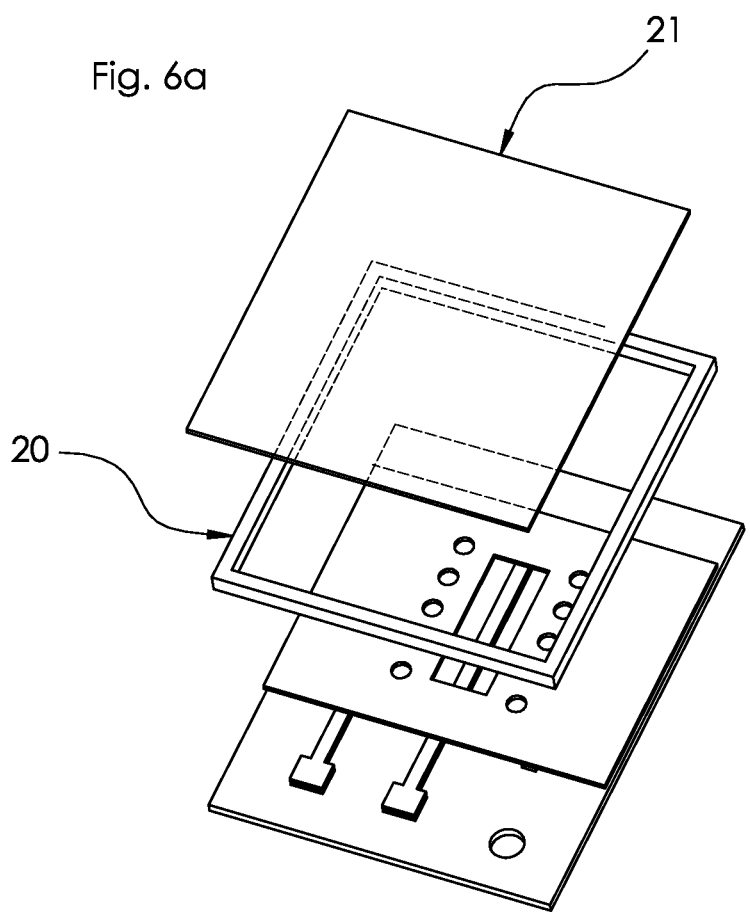
FIGS. 6a-6b schematically show a configuration of the electrophoretic chip of the present application. A thick dielectric layer 20 is printed as a frame at the outer perimeter of the chip, followed by placement of a transparent sheet 21 thereon, thereby creating a fluidic chamber or channel 22 for delivery of the tested fluid to the electrode structure.
Figure 6B:
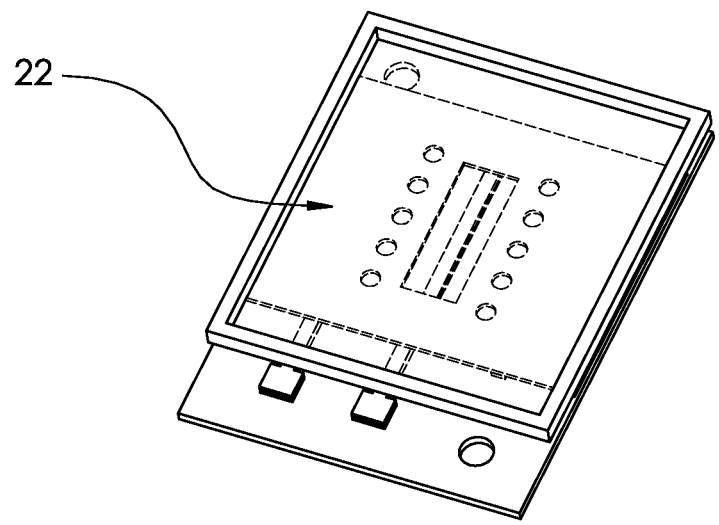

FIGS. 6a-6b show a configuration of the electrophoretic chip of the present invention, which further comprises a thick insulating layer of dielectric or bonded perforated material (dielectric layer) 20 placed on top of the electrophoretic chip. The thick dielectric layer 20 is printed as a frame at the outer perimeter of the electrophoretic chip or around the array of electrodes, followed by placement of a transparent sheet 21 thereon, thereby creating a fluidic or microfluidic chamber or channel 22 for delivery of the tested fluid to the electrode structure. In fact, the dielectric layer 20 forms boundaries of the fluidic chamber or channel 22. Liquid solutions to be tested enter the fluidic chamber or channel 22 through an inlet hole 11 and exit the chamber through an outlet hole 11' (shown in FIG. 2). The transparent sheet 21 placed on top of the fluidic chamber or channel 22 serves as a cover and makes it possible to measure optical signals (fluorescence, luminescence etc.) or perform any optical imaging within the fluidic chamber or channel 22.

The electrode structures of the electrophoretic chip disclosed herein can be manufactured in three configurations. Initially, low-resistance ink lines (conducting lines, e.g., silver ink lines), are placed on a non-conductive substrate. In the first configuration, carbon ink paste of the same resistance as disclosed above is printed on top of the conducting lines. In the second configuration, new carbon ink layer with even higher resistance and with the aforementioned optional additives preventing any side electroactive reactions on the electrodes surface (thereby, minimizing the oxygen and hydrogen evolution), covers all the conducting lines. The resistor carbon ink, filling only the space between each individual working electrode (the working area) and a contact line (the connecting area), with no underlying low-resistance ink, may be the same as the carbon ink printed on top of the low-resistance ink. In this particular case, only two carbon ink layers are needed, since the carbon ink layer actually serves as both the resistor ink and the dielectric layer. In the third configuration, an additional (third) carbon ink layer printed on top of the existing carbon ink layer is used as a resistor ink, but this would be similar as placing the dielectric ink (insulator) as the third layer.

During normal operation of the electrophoretic chip of the present invention, the analyte molecule having a given charge is attracted to the addressable locations over the working electrodes. In some embodiments, the at least one opening above the counter electrode may form an additional addressable location. Since the negative charge of the counter electrode is opposite to the positive charge of the working electrode, the addressable locations at the counter electrode will attract analyte molecules having the opposite charge compared to those analyte molecules, which were originally planned to be separated. Accordingly, the same addressable locations at the counter electrode can also be used to attract at least one more analyte having an opposite charge compared to the first analyte, thereby making it possible to separate and test at least two different analytes with a single electrophoretic chip. Alternatively, the addressable locations at the counter electrode may be activated by reversing the polarity of the applied voltage, wherein the working electrodes become the counter electrode, and vice versa. In some embodiments, polarity reversal is used to electronically wash the analyte accumulated on the working electrodes, and/or non-specifically bound onto specific probes in the accumulation microgel layer.

Figures 7A, 7B:
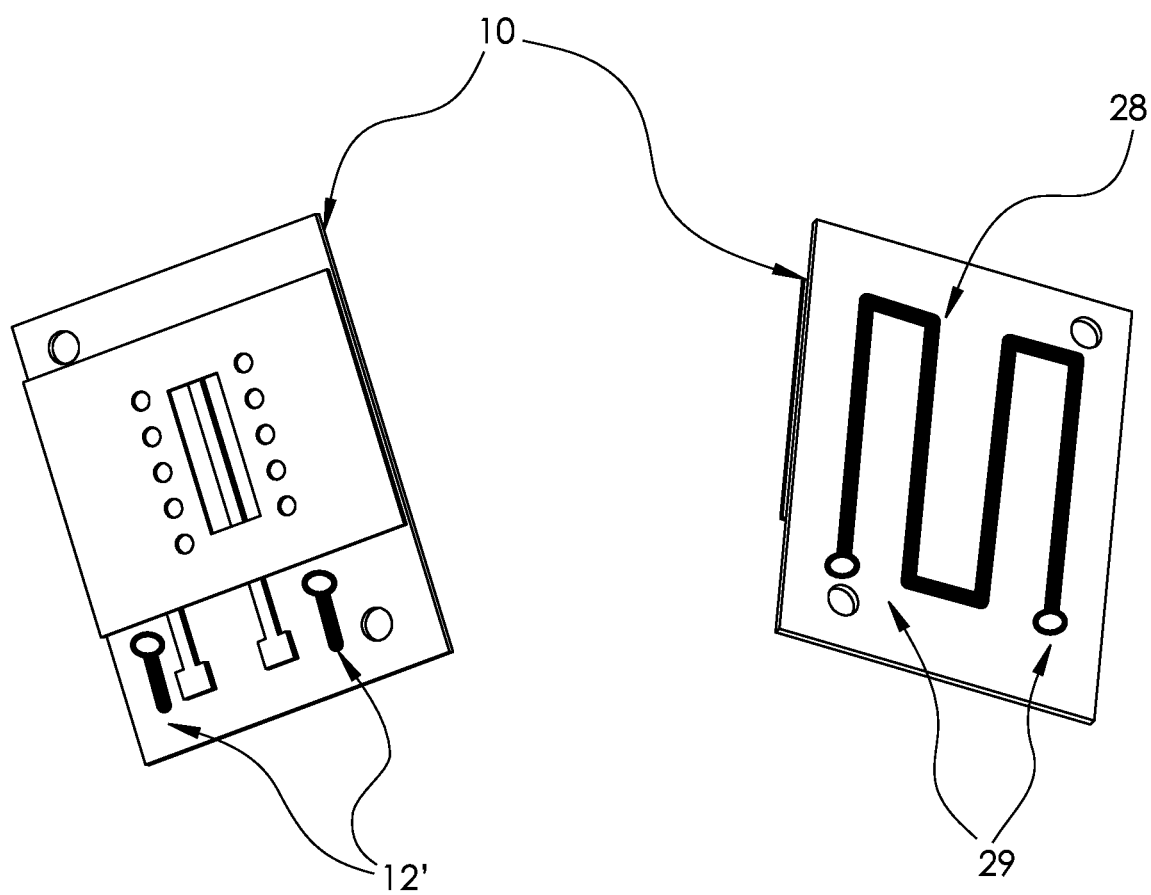
FIGS. 7a-7b schematically show the electrophoretic chip of the present application comprising high-conductivity ink heater layer 28 printed at the bottom of the non-conductive substrate 10. In this configuration, the non-conductive substrate 10 comprises through holes 29, through which the high-conductivity ink heater layer 28 extends to its contacts 12' printed on a top side of the non-conductive substrate 10.

In some embodiments, the non-conductive substrate further comprises a high-conductivity ink heater layer printed on a bottom side of the non-conductive substrate, as shown in FIGS. 7a-7b. In this configuration, the non-conductive substrate comprises printed-through holes 29, through which the high-conductivity ink heater layer 28 extends to its contacts 12' printed on a top side of the non-conductive substrate. In other words, printed-through holes 29 are used to bring the heater layer's electrical contacts 12' to the top side of the non-conductive substrate. This allows the heater layer 28 to contact the power source in a simple manner from the top side of the non-conductive substrate and obviates the need for additional electrical contacts from the bottom of the chip.

The high-conductivity ink heater layer 28 performs heating of the chip and of the fluidic chamber located on the opposite side of the chip over the entire non-conductive substrate where the meandering heater lines are located. This helps to remove most of the non-specifically bound analytes, thereby reducing the background noise and improving specificity and sensitivity of the electrophoretic method of the present application. In a particular embodiment, the heater layer 28 is not in contact with the conductive layer 23 or with the carbon ink layer 24, i.e., separated from them with a non-conductive substrate and has no electrical association therewith.

When the heater layer 28 is activated, the temperature of the tested solution is increased, thereby allowing enhanced transport of analytes in the solution to the addressable locations 19, or temperature-based removal of non-specific analytes, such as non-specifically bound DNA (in a DNA detection process), which could be washed away under higher temperatures.

In some embodiments, the heater layer 28 can be prepared from silver-based inks. It can also be prepared from the inks having physical properties identical or similar to those of the conductive low-resistance ink layer of the electrode structure. The heater layer 28 may be in the form of either a thick or thin film. Thick films are typically printed as distinguished from thin films which are frequently applied by a vapour deposition process. A thin-film heater element has high electrical resistance, due to its extremely thin cross section and the nature of the heater material. The heater layer may be made from the following exemplary materials: ceramic such as positive-thermal-coefficient ceramic, ceramic metal (cermet), polymers such as Kapton® (a flexible lightweight organic polyimide polymer thin film with high dielectric capabilities) and silicone rubber. Besides the ceramic-based pastes, polymer systems can also be applied to the fabrication of heater elements, allowing high flexibility with regard to substrate selection. The printed thick-film polymer heaters comprise low-resistance printed silver- or carbon-filled polymers acting as heater tracks. The conductive particles, such as silver and carbon are suspended within a polymer binder.

In some embodiment, other types of heating may be used instead of, or alongside with, the heater layer 28, such as an external heater (coil, Kapton® heater or similar) In another embodiment, through holes 29 can be used to fabricate electrophoretic chips with multiple-layer structures, namely not printing only on the non-conductive substrate, but printing two, three or more layers separated from one another by, e.g., an isolating or dielectric layer, where each particular printed layer is transferred or exposed to the next layer through such through holes. Thus, e.g., the heater layer may be embedded in the third layer of a four-layer structure, where the heater layer's contacts are brought to the top surface via through holes. In that case, the carbon electrode array can be placed in the first layer, optionally covered with a matrix, e.g., for electrophoresis purposes. Then, in the second layer, there will be carbon-based electrodes for electronic purposes, while in the fourth layer, various sensors and/or control arrays may be arranged.

Figure 7C:
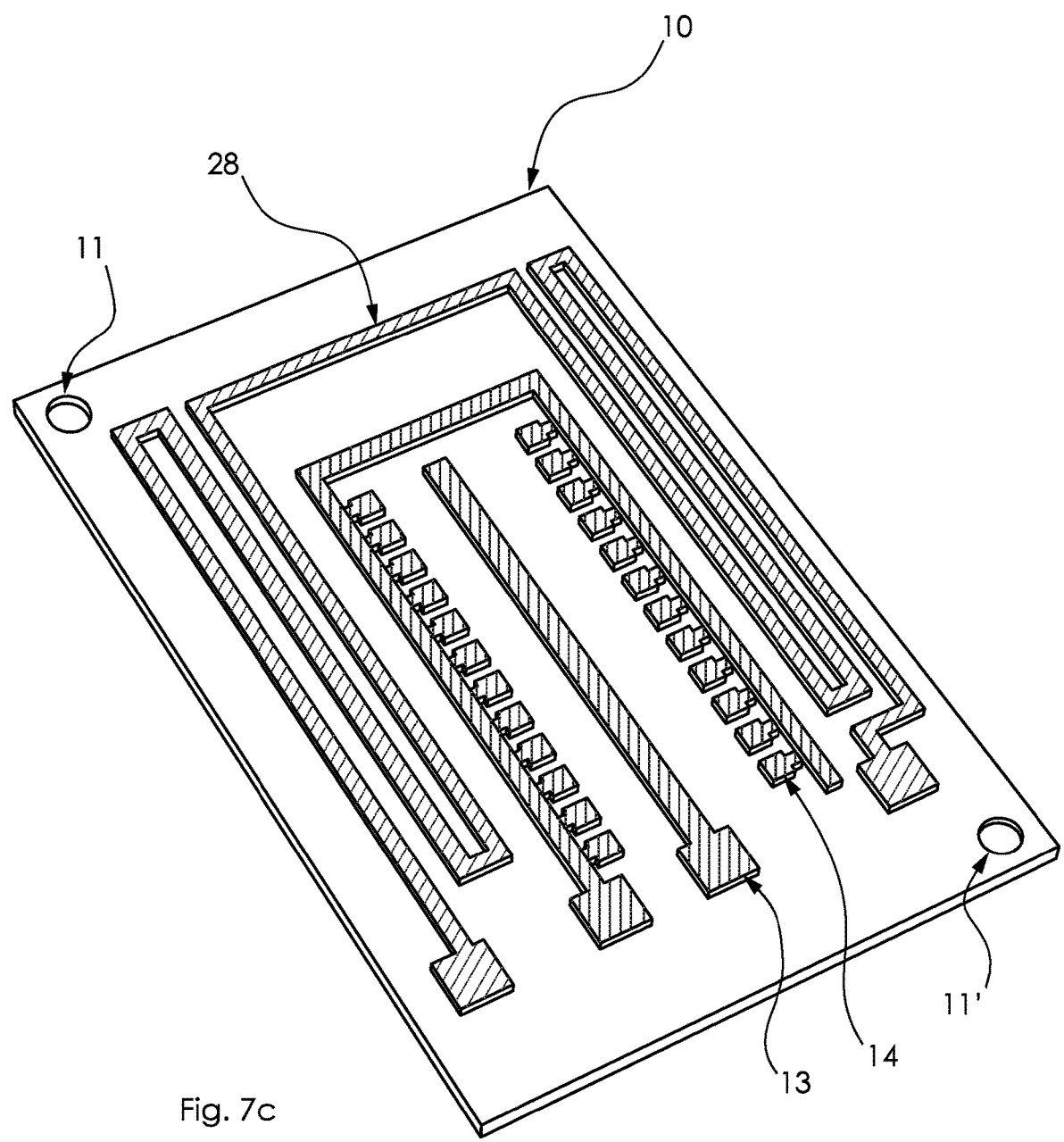
FIG. 7c schematically show the electrophoretic chip of the present application comprising the high-conductivity ink heater layer 28 printed at the top of the non-conductive substrate 10. Other elements of the chip shown in this figure are: 11—inlet printed-through hole, 11'—outlet printed-through hole, 13—counter electrode, 14—working electrodes.

An alternative configuration is shown in FIG. 7c, where the high-conductivity ink heater layer 28 is printed on the top of the non-conductive substrate 10, and is not in contact with the electrode structure.

Figure 8A:
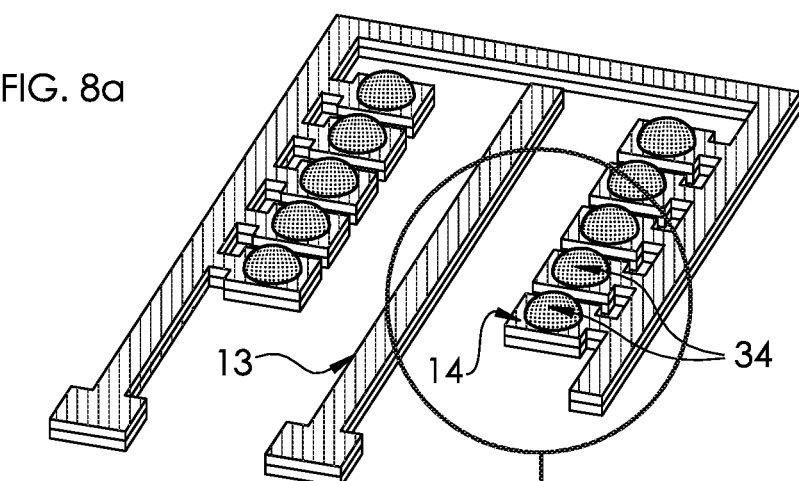
FIGS. 8a-8b schematically show a three-dimensional view of the electrophoretic chip of the present application shown in the previous figures, wherein each working electrode is covered with a single microgel 34 spotted on top of it.
Figure 8B:
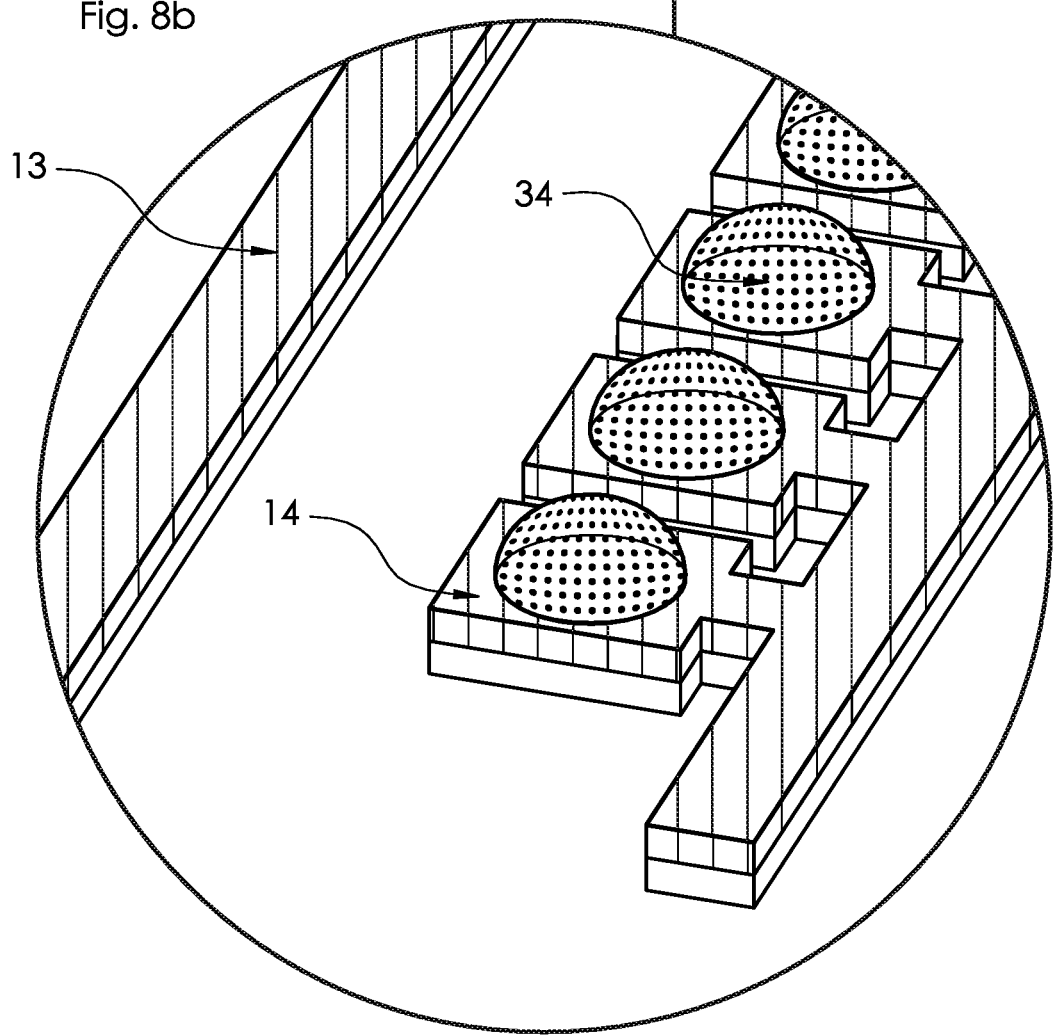

The molecule capturing matrix is spotted only upon addressable locations 19, as shown in FIGS. 8a-8b, such that adjacent spots on the matrix are not in direct contact with each another. This configuration of the matrix spots, defined herein as "microgel regions", enables much faster transport of analyte molecules to the electrodes as compared to the currently known electrophoresis devices having a bulk or monolithic block of gel that covers the entire surface of the electrodes. Since this configuration includes a gel-solution-gel (GSG) interface, it enables multiple accumulation spots or zones, when horizontal movement of molecules, like in gel electrophoresis, is promoted. The advantages of this configuration are summarised below.

As mentioned above, this matrix can be made from various materials, such as porous polymeric structures, film forming lattices, proteinaceous mixtures such as photo-formable proteinaceous mixtures, semipermeable solid films, gas permeable membranes functionalised with chemical functional groups, in order to form an attachment layer, coatings, or similar. The addressable locations may bind various analytes by, e.g., physical absorption to the surface, covalent binding to the surface via functional groups and/or cross-linkers and supported films. This will be described in more detail below.

Figure 9C:
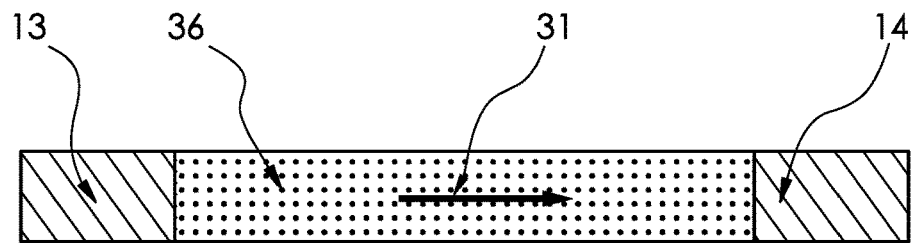
Figure 9C:
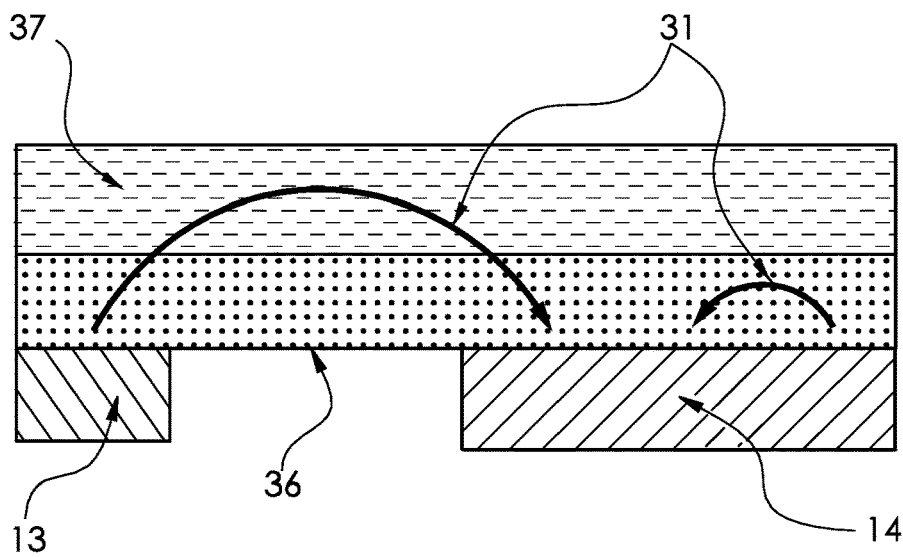
Figure 9C:
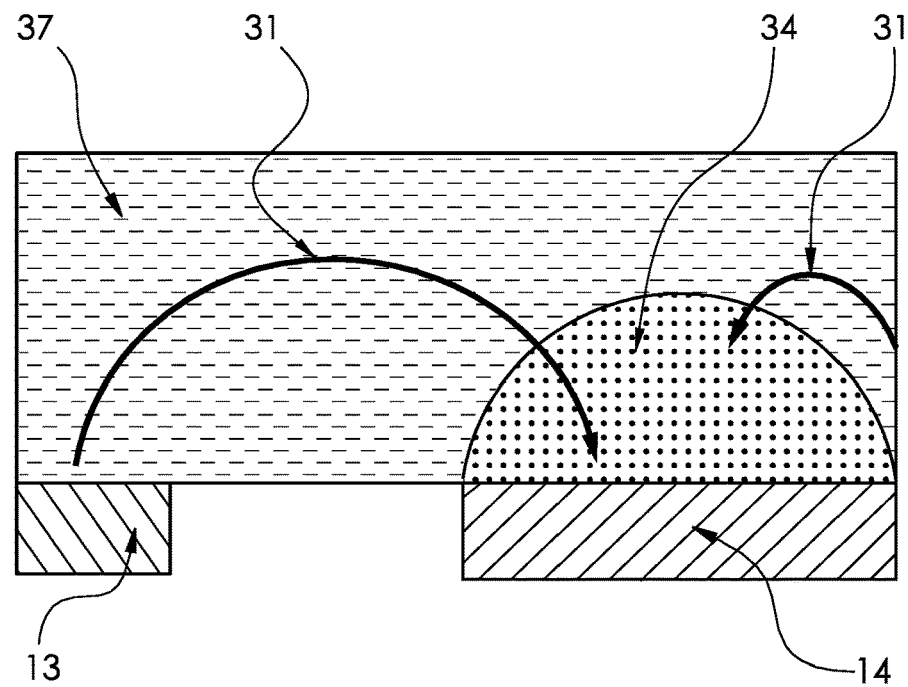

Gel-based electrophoretic devices known in the prior art use only electrode systems with a bulk gel layer for separation of molecules. These electrophoretic devices are schematically shown in FIGS. 9a, 9b and 10a, and compared with the electrophoretic chip of the present invention shown in FIGS. 9c and 10b. In contrast to the gel-electrophoretic devices currently known, the electrophoretic chip disclosed herein has a molecule capturing matrix spotted on and covering at least one addressable location, thereby creating at least one microgel region.

FIGS. 9a-9c schematically compare a gel-based electrophoretic device as currently known (see FIGS. 9a-9b) having a bulk gel layer 36 over the electrodes, and an electrophoretic chip of the present invention that has a molecule capturing matrix of microgels 34 over the array of electrodes (see FIG. 9c). As shown in FIG. 9c, microgels 34 are spotted onto each working electrode 14 of the array, where the analyte accumulation occurs, while the counter electrode 13 is not coated with the gel. This geometry is significantly different from that of the currently known chips, and enables significantly better analyte collection and transport between the counter electrode and working electrodes The analyte molecules are transported along the lines 31 formed once voltage is applied to the device as shown in FIGS. 9a-9c and 10a-10b. These lines are different in the devices currently known and the electrophoretic chip of the present invention, as will be discussed below.

As shown in FIGS. 9a and 9b, in the electrophoretic devices currently known, the entire electrode array is covered with a bulk hydrogel 36 forming a monolithic layer, where the analyte transport is significantly slowed down. In contrast, in the electrophoretic chip of the present invention (see FIGS. 8a-8b and FIG. 9c), a microgel is spotted directly onto each working electrode, covering only the surface of the electrodes and protruding into the solution for the thickness of the microgel, which is typically 5-500 μm, more preferably 30-150 μm. The microgels used in the electrophoretic chip of the present invention are not connected and do not form a monolithic layer as in a standard gel electrophoresis and in electrophoretic devices currently known. As a result, the tested solution 37 shown in FIG. 9c between the electrodes of the electrophoretic chip of the present invention is under a localised electric field, and the analyte molecules between the electrodes (and particularly at their surfaces) thus move through the solution rather than the gel, as in the currently known electrophoretic devices shown in FIGS. 9a and 9b. Since the transport through the solution is much faster than through the gel, the overall collection in the electrophoretic chip of the present invention is more efficient. The tested solution 37 shown in FIG. 9c is typically about 0.1-1.0 mm thickness.

The electrodes in the electrophoretic chip of the present invention are preferably positioned in a single horizontal plane. As a result, the electric field lines 31 (see FIG. 9c) pass through the tested solution 37 into the microgels 34. In other words, the electric field lines 31 at the working electrodes 14, which accumulate analyte molecules, are pointing toward the working electrodes, extending from the counter electrodes and from the entire solution volume above each working electrode in the array. Thus, each working electrode in the array is exposed to a uniform and high field (because of the layered electrode structure) and therefore, the collection from the solution volume above each one of the working electrodes in the array is identical.

FIGS. 10a and 10b illustrate three-dimensional views of an electrophoretic device currently known and an electrophoretic chip as disclosed herein, respectively. The known configuration having a bulk gel layer over the electrodes shown in FIG. 10a is compared with the present electrophoretic chip having microgels placed over the working electrodes of the array shown in FIG. 10b. Transport of the same analyte molecules 30 and 32 at the different distances to the electrodes through the gel is conducted. The molecules 30 and 32 shown in FIG. 10b become responsive to the electric field and are attracted along the electric field lines 31 toward the working electrodes 14 of the electrophoretic chip of the present invention.

Figure 11A:
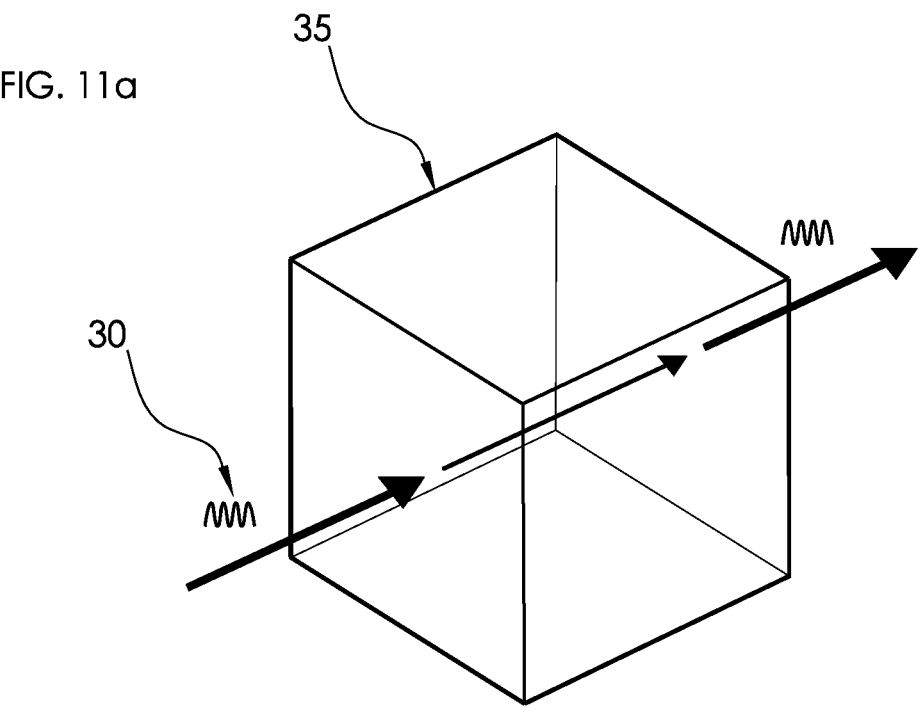
FIGS. 11a-11b schematically show electrophoretic transport of target molecules 30 through a liquid or solution medium 35 and through a bulk gel layer 36, respectively.
Figure 11B:
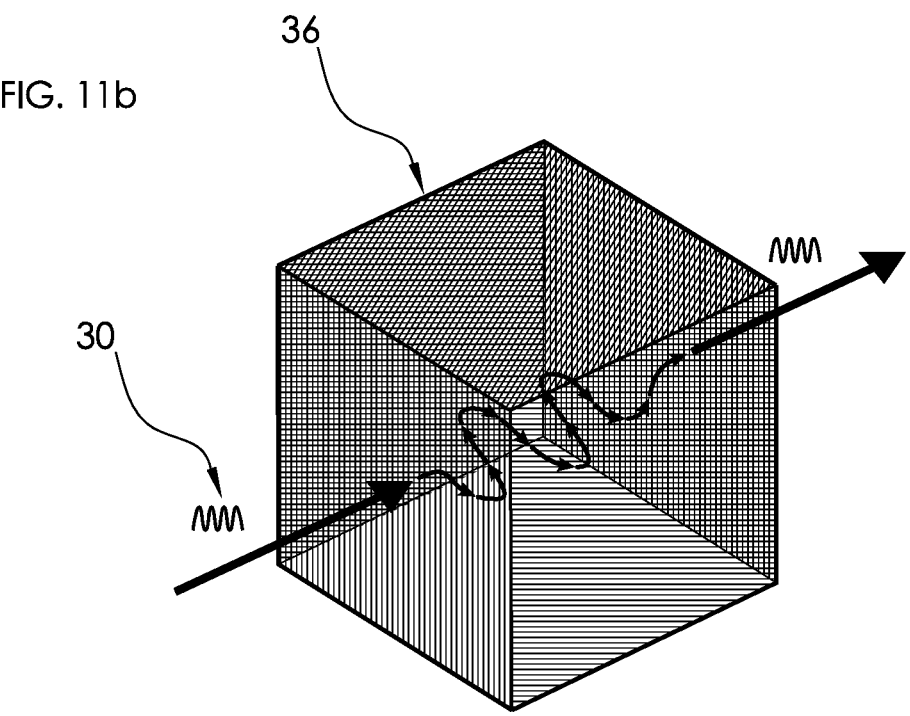

In this respect, it should be noted that the solid bold arrows actually indicate the movement and/or transport of the analyte molecules. So, the lines 31 shown in FIGS. 10a-10b schematically represent a combination of the electric field lines, position and shape of these field lines. However, the direction and length of these lines relate only to the transport of the analyte molecules. Therefore, these arrows in FIG. 10a are shorter through the gel, where the transport of the analyte molecules is considerably slower or less efficient, than through the solution. This is explained in FIGS. 11a-11b, schematically illustrating the electrophoretic transport of the molecules 30 through a liquid medium 35 and through a porous gel matrix 36, respectively. The porous gel matrix 36 impedes the transport compared to the transport in liquid. FIG. 11b demonstrates a slow, long, meandering pathway of the molecules 30 through the gel matrix, while FIG. 11a shows a straight forward, easier and faster transport through the liquid or solution medium.

When voltage is applied to the currently known electrophoretic device or to the electrophoretic chip disclosed herein, an electric field with the lines 31 is formed between the counter electrode 13 and each working electrode 14, as shown in the FIGS. 10a-10b. Analyte molecules 30 and 32, e.g., nucleic acids, are attracted along the lines 31 toward the working electrodes 14. If these analyte molecules 30 and 32 are negatively charged, the working electrodes 14 must be positively charged to accumulate the molecules 30 and 32 at the working electrodes surface. In general, the direction of the electric field is the direction of the force that would be exerted on a positive charge. Therefore, the arrows of the lines 31 point from plus toward minus.

The layered structure and resistive properties of the carbon inks used for printing the working electrodes or the resistor layer 25 (shown in FIG. 5) in the electrophoretic chip of the present invention makes it possible to achieve relatively high voltage between the counter electrode 13 and the working electrodes 14. The higher this voltage is achieved, the faster is the molecular transport, and the more efficient is the accumulation process of the analyte molecules 30 or 32 within the microgel matrix. The penetration and capturing of the analyte molecules in the electrophoretic chip disclosed herein does not occur through the entire gel structure, as in the currently known electrophoretic devices, but closer to the surface of the microgel, potentially at a 10%-50% depth of the microgel region, depending on the duration of the voltage applied.

Apart from the applied voltage, the parameters that control the electrophoretic chip of the present invention include the geometry of the electrodes, geometry of the spotted or deposited microgels, the spacing d between the counter electrode 13 and the working electrodes 14, and the spacing w between the working electrodes. The length of the lines and the size of the arrows that indicate the direction and the local velocity of the transported analyte molecule are dependent on the position or distance from the electrodes and on the medium, through which the analyte moves.

Figure 12B:
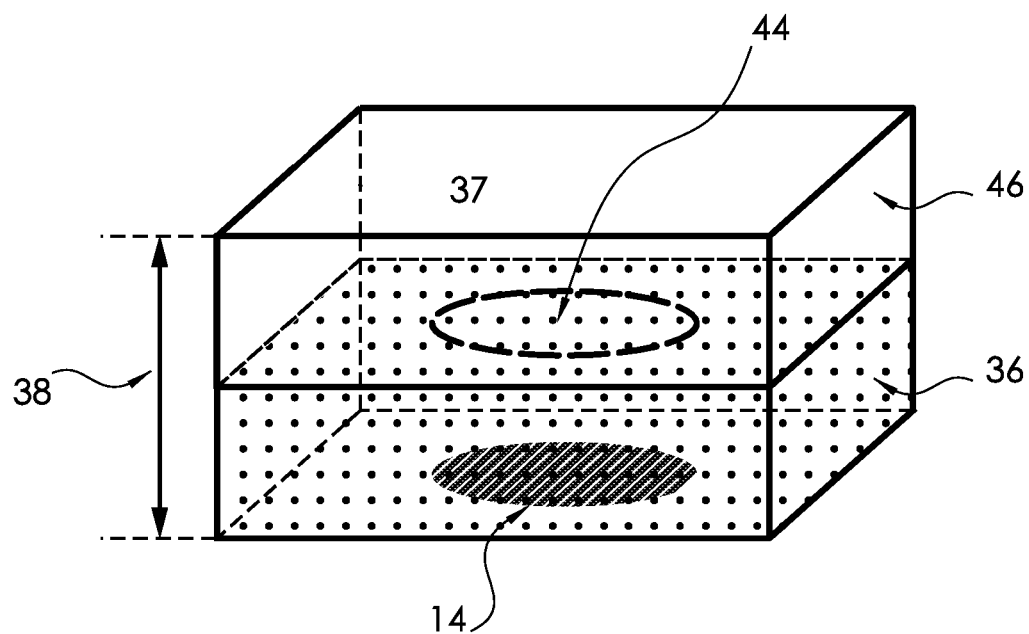
FIG. 12b schematically shows a 3D view of the working electrode 14 of the electrophoretic chip of the present application shown in FIG. 9c and FIG. 10b, having a microgel 34 spotted over the electrode.
Figure 12B:
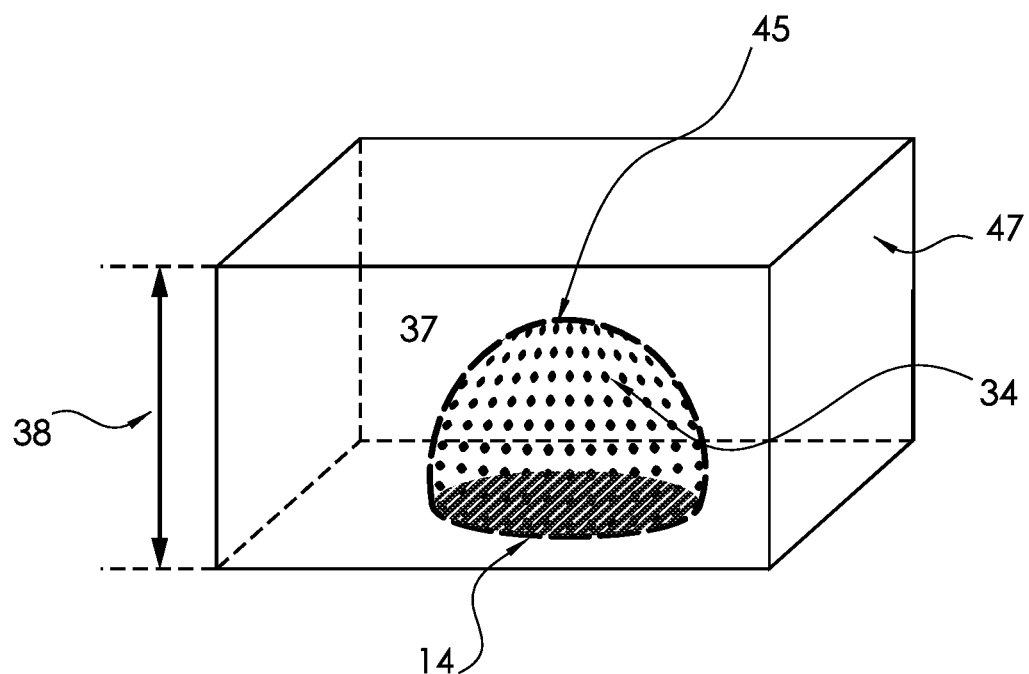
Figure 12D:
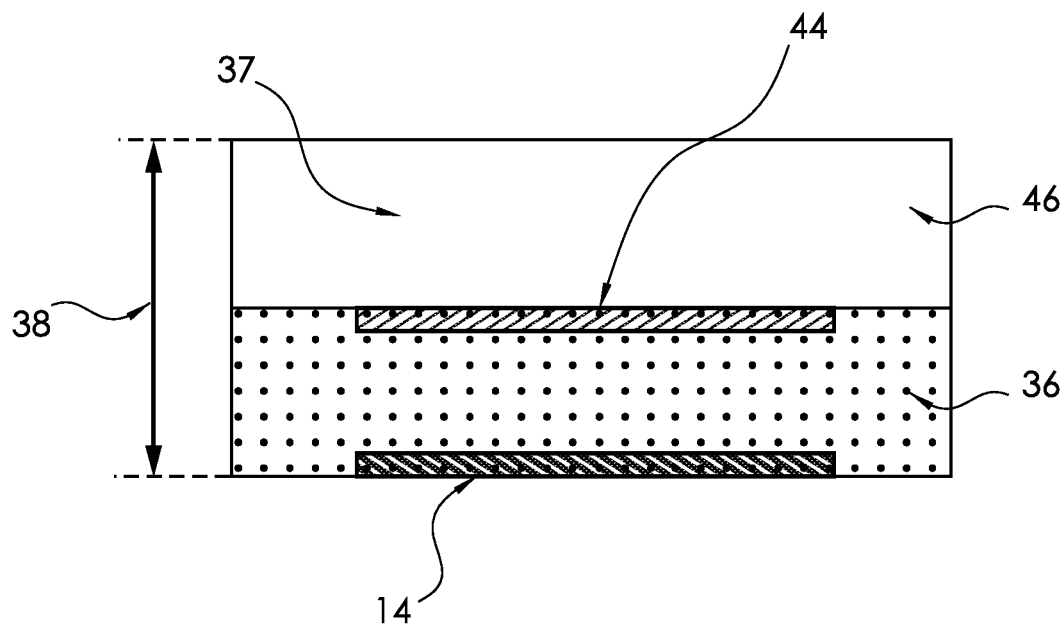
FIG. 12d corresponds to FIG. 12b and schematically shows a side view of the working electrode 14 of the electrophoretic chip of the present application shown in FIG. 9c and FIG. 10b and having a microgel 34 spotted over the electrode.
Figure 12D:
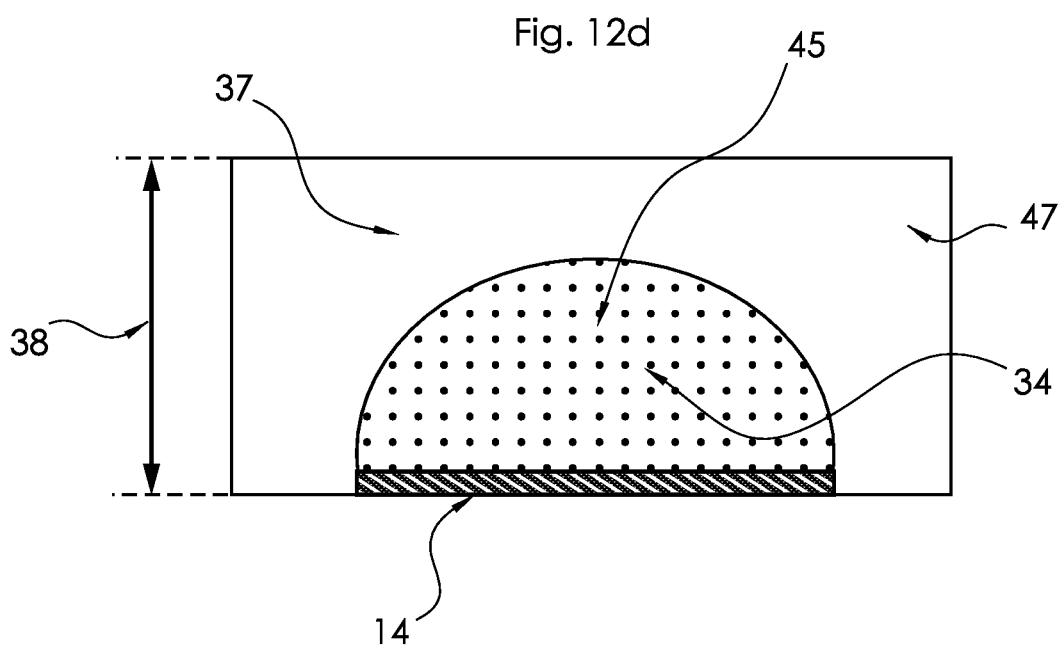

FIGS. 12a and 12c (corresponding to FIGS. 9b and 10a) show a 3D view and the side view of a working electrode in an electrophoretic device having a bulk gel layer 36 spread over the electrodes. FIGS. 12b and 12d (corresponding to FIGS. 9c and 10b), show a 3D view and the side view of a working electrode in an electrophoretic chip of the present invention, having a microgel globule 34 over the working electrode. These two pairs of figures serve to compare the efficiency of the electrophoretic accumulation of an analyte in bulk solution 37 between the two electrophoretic chips. The comparison is made by schematically showing the corresponding collection regions 46 (in the currently known device) and 47 (in the electrophoretic chip disclosed herein) of the analyte.

The term "bulk solution" as used herein with respect to the tested solution 37 refers to the whole tested solution in general, to differentiate it from a smaller volume of the solution in the vicinity of the electrode surface. Assuming that the bulk solution 37 forms a liquid "layer" of the analyte molecules above the electrodes within the fluidic channel 22 associated with the electrophoretic chip of the present invention (see FIG. 6b), the thickness of this solution layer would be the height 38 of the fluidic channel. This is simply because the fluidic channel is made of a thin sheet or frame entirely filled with the bulk solution 37. The same height 38 of the fluidic channel is assumed for the currently known electrophoretic device for comparison reasons. The term "collection region" is used herein to differentiate between the bulk solution and the part of it from which the analyte molecules are collected. As seen in FIGS. 12a-12d, the collection region 46 in an electrophoretic device having a bulk gel is very different from the collection region 47 in an electrophoretic chip having microgels as disclosed herein, leading to a completely different electrophoretic accumulation efficiency, as will be detailed below.

In the bulk gel configuration shown in FIGS. 12a and 12c, the surface area of the gel matrix 36, where the analyte molecules are collected, is schematically presented by circular planar surface 44 (in case the electrode is round-shaped). In the electrophoretic chip of the present invention, the surface area of the microgel globule is schematically presented in FIGS. 12b and 12d by hemi-spherical surface 45. The reason for the circular shape of the surface collection area will be explained below. Thus, whereas in the bulk gel chip configuration shown in FIGS. 12a and 12c, the analyte molecules are accumulated at the surface of the flat, bulk gel, e.g., within about 10% of the gel thickness from its surface 44, in the microgel configuration, the accumulation actually occurs on the hemi-spherical surface 45 of the spotted gel globule 34, e.g., within the same depth of about 10% of the gel thickness from its surface.

As shown in FIGS. 12a-12d, the actual volume of the bulk solution from which the analyte molecules are collected relates to the collection regions 46 and 47, which depend on the geometry and the volume of the bulk gel or microgel. In the microgel configuration illustrated in FIGS. 12b and 12d, the bulk solution 37 entirely "envelops" the working electrode 14 (surrounds it from all sides) and the collection occurs on the hemispherical surface 45 of the microgel globule. In contrast, in the bulk gel configuration shown in FIGS. 12a and 12c, the collection from the bulk solution 37 occurs only in the area above the gel layer spread over a working electrode. Therefore, the collection region 47 in the microgel configuration is much larger than the collection region 46 in the bulk gel configuration. This observation becomes even clearer by visual comparison of these collection regions shown in FIGS. 12a-12d. In the bulk gel configuration shown in FIGS. 12a and 12c, the bulk gel 36 covers the electrodes as a layer. The electric field formed after applying voltage in that case acts straight up from the round-shaped electrode surface through the gel 36 and forms a virtual column, thereby resulting in collection on the circular surface 44 of the gel layer at the gel/solution interface only. In contrast, in the microgels configuration shown in FIGS. 12b and 12d, the collection region 47 actually surrounds the electrode and the microgel hemisphere, and thus represents a much larger area under the influence of the electric field.

Thus, with the electrode diameter, spacing d and w between the electrodes, as shown in FIG. 10b, and the same height 38 of the fluidic channel, based on the gel geometry only, the electrophoretic chip of the present invention may accumulate twice the amount of the tested analyte than the electrophoretic chips currently known. For example, in the bulk gel configuration, the circular surface area 44, where the collection occurs, is equal to $\pi r^2$, where r is an electrode radius, whereas in the microgel configuration, the hemispherical surface 45, where the collection occurs, is equal to $2\pi r^2$. The area 45 is therefore twice as large as the area 44, for the same radius of the round-shaped electrode. The same result is obtained if one compares the volumes. This clearly demonstrates significantly larger accumulation of the analyte molecules on the microgels configuration compared to the bulk gel configuration, based on their geometry only, where all other parameters are kept the same.

The application of the nanometre electrodes having the nanometre microgel regions may be useful in electrophoretically controlled or driven self-assembly of nano-elements. Also, the electrophoretic chip of the present invention with the spotted microgels is superior over the bulk gel electrophoretic device because of the vertically radial electrophoretic movement of the analyte molecules and their downward accumulation in multiple microgels.

FIGS. 13a and 13b compare a side view of a currently known electrophoretic device (FIG. 13a) with that of the electrophoretic chip of the present invention (FIG. 13b). Both configurations have a (negative) counter electrode 13 and an array of working electrodes 14 positioned in a single plane. Each working electrode has the same diameter 41. The known configuration having a bulk gel layer over the electrodes, as shown in FIG. 13a, is compared with the present electrophoretic chip having microgels placed over the working electrode, as shown in FIG. 13b. The fluidic channel height 38 is assumed to be the same in both cases, in order to be able to compare the efficiency of the electrophoretic transport and the accumulation of the analyte molecules. Above each working electrode, the transport of the analyte molecules 30 (e.g., negatively charged analyte molecules) occurs from the bulk solution 37 toward the positively charged working electrode 14. As described above, the volume of the bulk solution 37 above each working electrode 14 can be determined by the diameter or dimensions of the working electrode and the fluidic channel height 38.

Since the bulk gel layer thickness 39 in the configuration shown in FIG. 13a may present a substantial portion of the fluidic channel height 38, the volume of the collecting region 46 in this case can be determined as a mathematical product of the following parameters:

thickness 42 of the solution bulk layer 37 above the gel layer 36, width 40 of the fluidic channel, within which the effective electric field is formed around the electrodes, and the electrode diameter 41, providing that the electrode has a round shape, or any other dimension of a non-round electrode.

For the microgel-based configuration shown in FIG. 13b, the volume of the collecting region 47, from which the analyte is collected and accumulated at the working electrode 14, can be determined as a mathematical product of the of the following parameters:

the fluidic channel height 38, the width 40 of the fluidic channel, and the electrode diameter 41, providing that the electrode has a round shape, or any other dimension of a non-round electrode.

The volume of the microgel globules (or hemi-spherical columns), though small, should then be subtracted from the above calculated volume to get the actual volume of the collecting region 47, from which the analyte is collected and accumulated at the working electrodes.

Thus, based on the comparison of the geometries only, the volume of the analyte solution, from which the analyte is accumulated on the working electrodes, is larger in the electrophoretic chip of the present invention. Thin fluidic channels having their height 38 comparable to the height 43 of the microgel columns may result in a highly efficient collection of the analyte at the working electrode 14. This is corroborated by the known fact that the electric field is stronger and the molecular transport is faster at a closer distance to the electrodes (in the vicinity of the electrode surface or directly between the counter electrode 13 and the working electrode 14). The collection of the analyte molecules 30 and their transport occurs from the bulk of the tested solution 37 toward each working electrode 14. The analyte molecules 32 (see FIG. 13b) found near or between the electrodes are therefore transported and collected at much faster rates than the analyte molecules 30, as will be discussed below.

The aforementioned prior-art design of electrophoretic in-plane array chips is based on a very thin bulk gel layer (about 5-10 μm). The design tendency in the prior art is to make the gel layer even thinner in order to easily remove (wash) non-specifically bound molecules including fluorescence reporters. Based on the above analysis, the recommended thickness or height of the fluidic channel for such chips should be about 20-50 μm. However, this extremely small channel size may pose very serious problems of the fluid transport through an extremely small fluidic channel, and may require very high pressures to transport the analyte solution through the fluidic device. Such high pressures could affect the stability of the bulk gel and potentially remove it from the chip. In contrast, the spotted microgels in the electrophoretic chip of the present invention are extremely small in volume but thick (having thickness of the globule about 5-500 μm that is larger than the electrode diameter) relatively to the bulk gel and thus protrude into the fluidic channel and efficiently capture the analyte molecules there.

As mentioned above, the transport of the analyte molecules is faster through the liquid than through the gel matrix where it is impeded by the pores and depends on their size in the gel matrix. It is well known that larger a molecule is, the slower is its transport through the electrophoretic gel matrix. As mentioned above, in the case of the bulk gel configuration, the analyte molecules are collected only on the circular planar surface 44 of the bulk gel layer above the electrodes. Assuming that the fluidic channel height 38 is constant in both configurations as shown in FIG. 13a-13b, the volume of the tested solution, from which the analyte molecules are pulled and transported toward the gel and working electrodes, is much smaller in the case of the bulk gel layer configuration than in the case of the microgel configuration (compare volumes 46 and 47 in FIGS. 13a and 13b, respectively). Choosing the fluidic channel height 38 to be very small, e.g., twice the diameter of the working electrode 14, the ratio between the solution volumes 47 to 46, as explained above, becomes about 4:1. This further indicates that in the microgel configuration of the electrophoretic chip of the present invention, the volume of the tested solution which is addressed above each electrode may be at least four times larger compared to that in the bulk gel layer configuration. Of course, for a direct comparison of accumulation of analyte molecules based on the volume of the solution addressed above each electrode, or from which the analyte molecules are pulled toward each working electrode, all the geometries and electrical parameters must be kept the same in both cases.

FIGS. 13a-13b demonstrate another advantage of the electrophoretic chip disclosed herein, referring to the electrophoretic accumulation of the analyte from the solution. FIG. 13a shows lines 31 and transport of the analyte molecules 30 with arrows in the prior-art bulk gel layer configuration. These arrows indicate efficient transport and accumulation occurring mostly vertically down, or only from the region directly above the electrode and its bulk gel matrix 36. As mentioned above, the length of the arrows 31 representing the electric field indicates the local transport velocities of the analyte molecules. In the bulk gel, these arrows become much shorter, indicating an impediment of the transport of the analyte molecules 30. In particular, these arrows 31 become very short directly between the counter electrode 13 and the working electrode 14 in the bulk gel configuration shown in FIG. 13a indicating inefficient transport or even lack thereof. In such cases, when the distance of the transport is very short, strongest electric field is determined only by spacing between the electrodes. As a result, the horizontal and downward transport from the side of the electrode is not possible, since no solution is present in the region that is covered with the gel.

In contrast, in the microgel configuration shown in FIG. 13b, the transport of the analyte molecules from that area, i.e., from the sides of the working electrodes, and in the vicinity of the electrode plane, is much faster due to the stronger electric field around. Accumulation from this region is much faster and more efficient than from the solution vertically above the electrode or gel matrix. In fact, the analyte molecules are pulled in from the bulk of the solution above this region and replenish quickly, since the actual transport occurs through the liquid only. The microgel matrix 34 is therefore spotted so that the globule diameter would be just slightly larger than the diameter of the electrode. This could be in the range of 10%-30% larger than the diameter of the electrode. The thickness of the spotted hemispherical gel globule should be approximately up to 2-3 times the electrode diameter. Therefore, the microgel thickness on the side of the electrode is about 2-3 times smaller than above the electrode, and therefore the electric field from the side of the electrode is much stronger. In contrast, in the bulk gel layer configuration, accumulation from the top (above the electrodes) occurs from a distance that is equal to the thickness of the gel; however, the electric field at that distance becomes relatively weak, and the transport is significantly reduced.

In some embodiments, the analyte molecules above the electrode structure and above the microgels of the electrophoretic chip of the present invention may be detected using fluorescence techniques. The fluorescence detection can be performed vertically from above the chip, wherein and the accumulated analyte molecules are visualised using a fluorescently labelled reporter that is attached to the captured analyte molecules. It is well known that the fluorescence detection integrates all the signals in a gel matrix. Since the accumulation of the analyte using the electrophoretic chip of the present invention occurs at a larger surface area, the hemispherical surface, but with about the same radius of the electrodes as in the bulk gel layer configuration, the fluorescence signal from the electrophoretic chip of the invention is much higher than that from the bulk gel. Fluorescence measured from the electrophoretic chip disclosed herein may therefore be enhanced due to:
1) A larger surface area of the microgels compared to the bulk gel layer configuration;
2) A larger volume of the analyte solution that is addressed on each working electrode and from which the analyte is attracted toward the working electrode; and
3) Stronger electric fields and more efficient transport of the analyte molecules in the microgel regions, in particular from the side and in the vicinity of the electrode plane surrounded by the strongest electric field.

The microgel globules may be spotted manually or using a robotized spotter, such as contact-pin spotting or sprayer spotting, or any other similar method for depositing gels and/or matrices with volumes in the range of about 10-200 nL. In another embodiment, the microgels may be formed in a shape of tall cylinders protruding into the tested analyte solution and approaching the fluidic channel height 38, thereby increasing efficiency of the accumulation. The gel matrix having a cylindrical shape or similar geometry enhancing the collection of analytes may be achieved using micro-molding methods. Thickness of the fluidic channel in this embodiment should not exceed 5×d (five times the distance between or from the electrodes).

In a further embodiment, multiple substrates with multiple arrays printed on different substrates may form two-sided electrophoretic arrays, or multi-chambers with vertically stacked electrode structures, possibly connected through the fluidic channels for electrophoretic accumulation or separation of different target analytes in the corresponding different chambers or fluidic cells. In a specific embodiment, two mutually opposite facing electrophoretic chips having the microgels protruding into the tested solution may be combined in a sandwich-like electrophoretic device configuration to enhance the transport, collection and accumulation of the analyte on both electrophoretic chips. Analyte molecules on both chips may be detected electrochemically or spectroscopically.

In yet further embodiment, the electrophoretic chip of the present invention may comprise tall three-dimensional electrodes having a cylindrical form printed over the substrate with carbon inks and protruding into the tested solution. In such case, the microgels may coat the surface of the three-dimensional electrodes following their shape. An advantage of such a configuration is that the microgels are uniformly spread around each electrode and allow high collection efficiency on the entire electrode surface. This configuration may further optimise the electric field distribution throughout the fluidic channels and thereby enhance accumulation of the analyte molecules from the tested solution by adjusting the shape and size of the three-dimensional electrodes.

The electrophoretic chip of the present invention may be used in combination with post-analytical methods for the detection of the analytes accumulated on the electrodes of the electrophoretic array. These post-analytical methods may be spectroscopic, such as various fluorescence methods, Raman scattering, or surface plasmon resonance based methods for detection of signals specific to a particular target analyte. However, other post-analytical techniques including electrochemical detection may also be combined with the method of the present invention.

EXAMPLES

Example 1: Controlling and Increasing the Electric Field on Arrays Made with Carbon Ink Layers of Different Resistivity The conductive layer 23, the carbon-ink layer 24 and the resistor layer 25 of different sheet resistivity were deposited in a geometry and arrangement as illustrated in FIGS. 2 and 6. A low-salt buffer electrolyte, used for electrophoretic accumulation and addressing of analytes, e.g. DNA onto the array, 50 mM histidine, was dispensed in each separate experiment over four working electrodes and the counter electrode between them, so that the geometry of the covering liquid with respect to the electrodes was kept constant in each experiment. A constant current of 0.5 mA was applied using a constant current power source at the electrode contacts to determine the voltage that was needed to pass this current through the layered carbon-ink structures caused by the electrode resistivity due to materials used, their composition and resistances, or overpotentials, at the electrode-electrolyte interface. Since the electrode reactions at the surface were the same in all experiments, the voltage was mainly determined by the electrode composition and structure. The basic inks used in this example were purchased from DuPont (USA), Henkel (USA) or CMI (Creative Materials Inc., USA).

TABLE 1

Control of the electric field in the electrophoretic process over an array using carbon ink layers and their mixtures as electrode materials

| | | Conductive ink layer (23) | Carbon ink layer (24) | Resistor layer (25) | Current (mA) | Voltage (V) |
|---|---|---|---|---|---|---|
| Experiment 1 | Ink Type | Henkel 479SS | DuPont 7102 | DuPont 5085 | 0.5 | 3.2 |
| | Sheet Resistance (Ω/square/mil) | 0.02 | 30 | 0.120 | | |
| Experiment 2 | Ink Type | Henkel 479SS | DuPont 7102 | DuPont 7102 | 0.5 | 6.5 |
| | Sheet Resistance (Ω/square/mil) | 0.02 | 30 | 30 | | |
| Experiment 3 | Ink Type | Henkel 479SS | DuPont 7102 | CMI 101-80 | 0.5 | 15.2 |
| | Sheet Resistance (Ω/square/mil) | 0.02 | 30 | 25,000 | | |

Table 1 clearly demonstrates the control over the electric field resulting from different compositions and/or layering of the carbon ink electrode structures. Keeping the current constant through the solution over the array, and for the same geometry between the electrodes and electrolyte added, the voltage required to drive the current was increased for approximately five times. The electric field, obtained by dividing the applied voltage by the distance between the electrodes would consequently increase for five times as well. No metal electrode would result in such a high field, our experiments demonstrated that if platinum electrode were used in a similar geometric arrangement, the voltage, with the same electrolyte would yield about 2.6 V between the working and counter electrodes. Therefore, water hydrolysis seems to be the dominant reaction. But on the carbon ink electrodes, it is further suppressed. Therefore, the main difference between carrying out the electrophoretic process with the electrophoretic chip of the present application and with the conventional electrophoretic devices using platinum electrodes is that the electrophoretic process with the instant electrophoretic device were controlled and performed in the significantly increased (five times) electric field compared to the metal electrodes.

As mentioned above, the total transport of charged species in solution, in terms of ionic and charged analyte transport, corresponds to the total current passed through the solution. However, ions, being small in diameter move easier and faster than the large molecules, therefore contributing to the total current much more than the transport of the analyte. Under conditions of higher voltage applied, the transport of large molecules is accelerated, and the molecules would move faster not only through the gel matrix, which is significantly impeding their transport, but also through solution. As disclosed in the present application, molecules may accumulate in hydrogels spotted over each working electrode. Therefore, both the transport through solution and through gels is enhanced.

Voltage and/or electric field may be varied either by combining ink properties, such as ink composition, geometry and disposition in the electrode array structure, or by combining inks of different resistivity in the same formulation, e.g., DuPont 7082 carbon inks with silver-based inks DuPont 5028 and dielectric inks DuPont 3571. In addition, this can be done by preparing some custom-made mixtures with precisely determined sheet resistivity and achieving the desired and controlled electric field values.

Example 2. Preparation of Electrode Arrays with Controlled Resistive Structures

The electrode arrays were prepared in accordance with the designs illustrated in FIGS. 2 and 6. In particular, the resistor layer 25 was printed using modified inks so that each electrode had an increased resistance as compared with the other. For a successful device manufacturing, it is critical to demonstrate that the resistive properties of each electrode are reproducible, and that the method would satisfy reproducible and potentially quantitative electrophoretic transport and accumulation of analytes at the electrode array. For that purpose, resistance was measured in a dry state after the electrode arrays were prepared.

Figure 14:
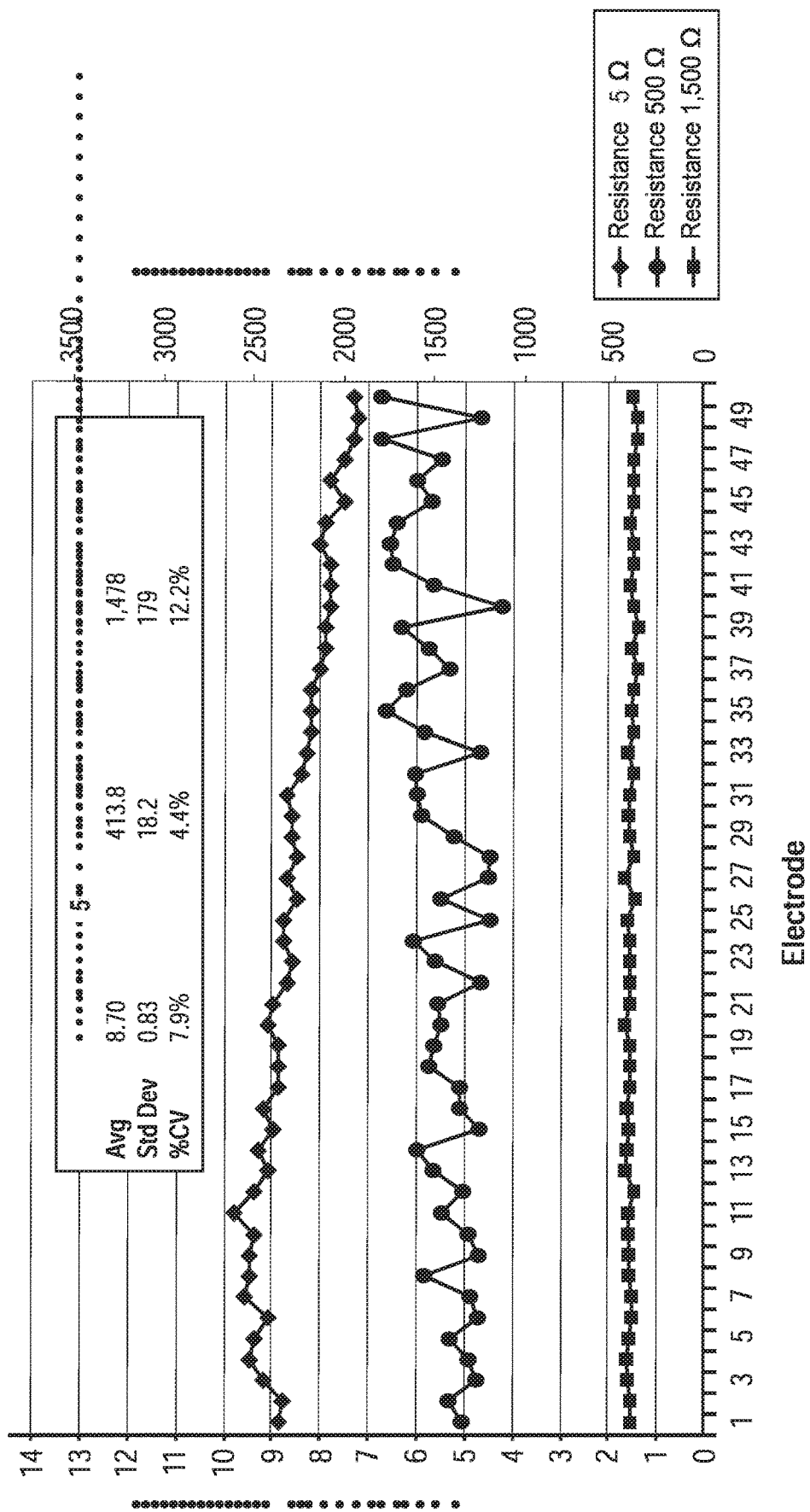
FIG. 14 shows the results of preparation of carbon-ink layered electrodes and of the electrophoretic chip of the present application in terms of uniformity of the resistor layers 25 that yields reproducible resistance values for each electrode in the structure. Three carbon-ink layered compositions with the same geometry as shown in FIGS. 2 and 6 were printed and tested.

FIG. 14 shows the results of preparation of carbon-ink layered electrodes and electrophoretic chip of the present application, in terms of uniformity of the resistor layer 25, that yields reproducible resistance values for each electrode in the structure. Three carbon-ink layered structures with the same geometry as shown in FIGS. 2 and 6 were printed and tested. The resistance was measured using an industrial multimeter, such as Fluke 87, and contacts were made at the beginning of the electrode lines and by touching the carbon-ink electrode surface.

The electrode arrays having resistance 5Ω and 500Ω had electrode ink compositions similar to those shown in Table 1 for Experiments 1 and 2. The electrode array having resistance 1,500Ω was similar in design to the Experiment 3 shown in Table 1, however the ink used was modified to exhibit the sheet resistance about 100,000 Ω/square/mil. It should be noted that the sheet resistance measured does not correspond to the sheet resistivity of the resistor layer 25, simply because sheet resistance value is defined similarly as in metal conductors by their geometry, i.e. by their surface area (width×length) and thickness of the layer. The current flowing during the measurements is a constant current. The experiment shows a uniform distribution of the current through the conductive layer 23.

This experiment was aimed at preparation of the electrophoretic electrodes of the present application that would exhibit around 5 Ω, 500Ω and 1,500Ω resistance along the working electrode-layered ink pathway. FIG. 14 shows the data obtained using these three configurations. The standard error in resistance for 50 electrodes tested on each electrode array was 7.9% for 5 Ω, 4.4% for 500Ω and 12.1% for 1,500Ω resistive inks located in the screen-printed electrode chip structure near each working electrode. The obtained results show the good reproducibility of the resistance measurements for the tested screen-printed electrode chips of the present application.

Example 3. Testing Optical Properties of Printed Carbon Ink-Based Electrophoretic Chips The electrophoretic chip of the present application may use optical detection and identification and detection of the analytes. In the present example, polyacrylamide-based microgels are spotted using robotised spotting over each electrode to enhance the capturing, accumulation and the fluorescence signal on the electrode array, measured post-electrophoretically.

Therefore, the printed inks (and all components of the electrophoretic chip including substrates) should be preferably and desirably made black in colour (which is not always possible) to minimise background fluorescence. In particular, the components of the electrode structure of the present application based on dielectric inks tend to exhibit higher autofluorescence than the black carbon-based inks.

Figure 15:
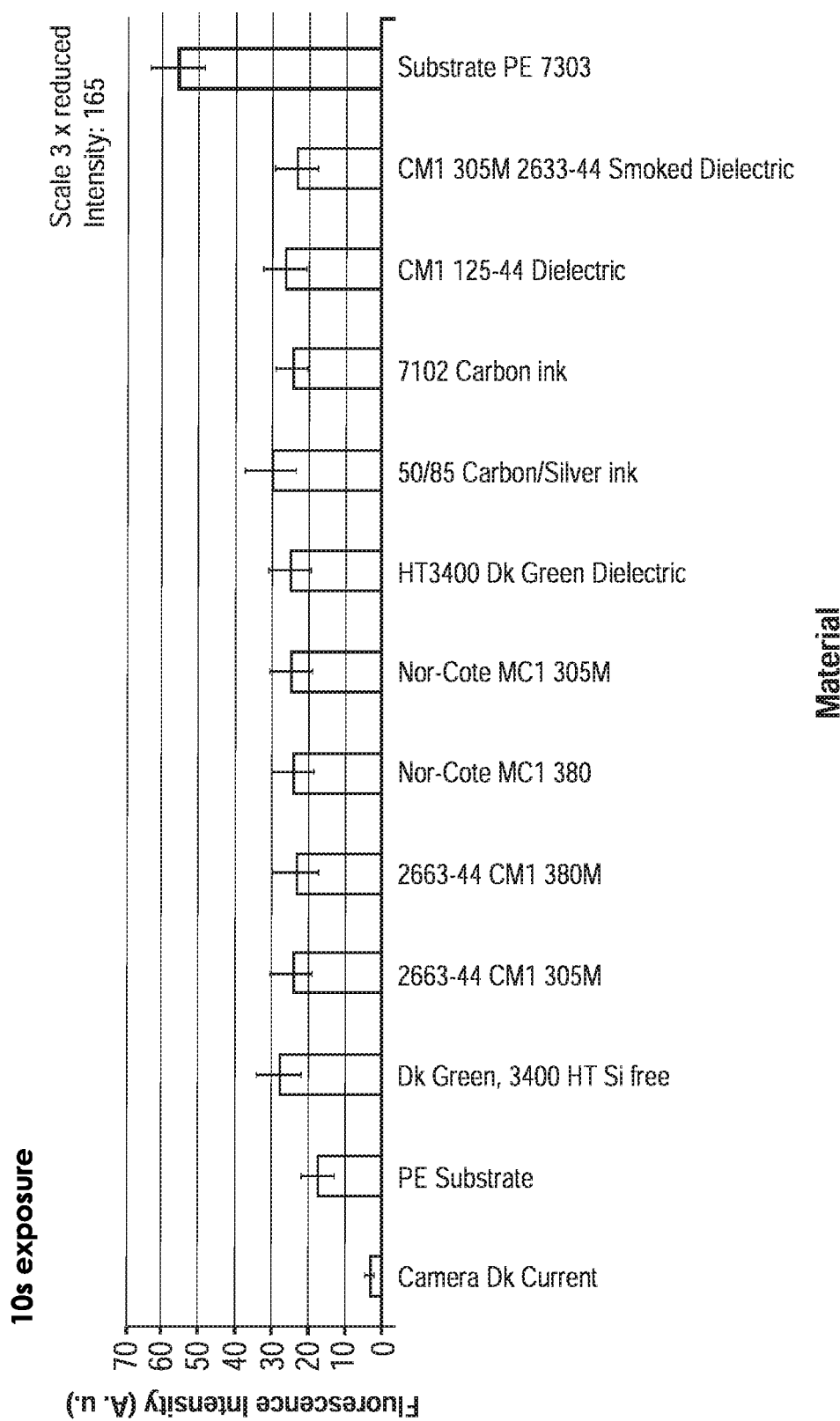
FIG. 15 summarises the data for autofluorescence of the exemplary printed chip materials, including dielectric inks, carbon inks, silver inks and substrates, used in the preparation of the electrophoretic chip of the present application.

FIG. 15 summarises the data for autofluorescence of the exemplary printed chip materials, including dielectric inks, carbon inks, silver inks and substrates, used in the preparation of the screen-printed electrode chip of the present application. This data was obtained using a portable fluorescence recorder within the MDx DNA detection system including filters for the camera and for the red LED illumination. Red fluorescence emission was observed and measured.

The data in FIG. 15 shows an example of a substrate that exhibited extremely high autofluorescence with the emission intensity about eight times higher than that of any of the inks. The data is exemplary for a range of materials including dielectric inks, carbon inks and conductive silver inks that were prepared and exhibited rather satisfactory low fluorescence background (except the PE 7303 polyester substrate).

Example 4. Electrophoretic Accumulation of DNA Molecules and Fluorescent Detection of the Specific DNA Sequence on the Electrode Array Analyte molecules, e.g., large charged biomolecules, such as DNA and RNA sequences, or proteins can be accumulated on the electrode array and detected using specific capture probe oligonucleotides embedded within the microgels spotted on top of each electrode of the electrode array of the present application. A 35-bp biotinylated capture probe was designed to be complementary to a 5-bp DNA target. Cy5, fluorescently labelled red reporter had a complementary sequence to the target, so that the target, if specifically captured onto the array gels could be detected using fluorescence spectroscopy. A non-complementary capture probes were prepared as well and addressed to locations to serve as a control for specificity of target binding to the specific probes only.

The experiment was carried out with the screen-printed electrode array chip, which construction and composition are described in Experiment 2 in Table 1 (other configurations exhibited similar positive results). 30 nL of (bis) acrylamide hydrogel was spotted onto each electrode and cured under UV light exposure for 10 seconds. The electrode arrays were washed with 50 mM histidine, dried and used in the experiment. The biotinylated capture probes (at 1 µM) were deposited at about 100-200 nL over each gel, and further deposited by diffusion within the hydrogel for 15 minutes. The electrophoretic chip of the present application was assembled, followed by introduction of the target DNA solution into the fluidic cell (ca 200 µL) of the device. In this experiment, the concentration range of the DNA target was 0.1-100 nM.

The target analyte was addressed at a constant current of 0.8 mA for 2 minutes. Non-specifically bound target molecules were washed with three washes in low-salt buffer phosphate (50 mM buffer phosphate, pH 7). The electrode array was then illuminated for two seconds (exposure time) using red LEDs with mounted narrow red filters, followed by detection with a camera having a narrow emission filter corresponding to the emission of the Cy5 dye. Obtained fluorescence intensity data was analysed using Image J software.

Figure 16:
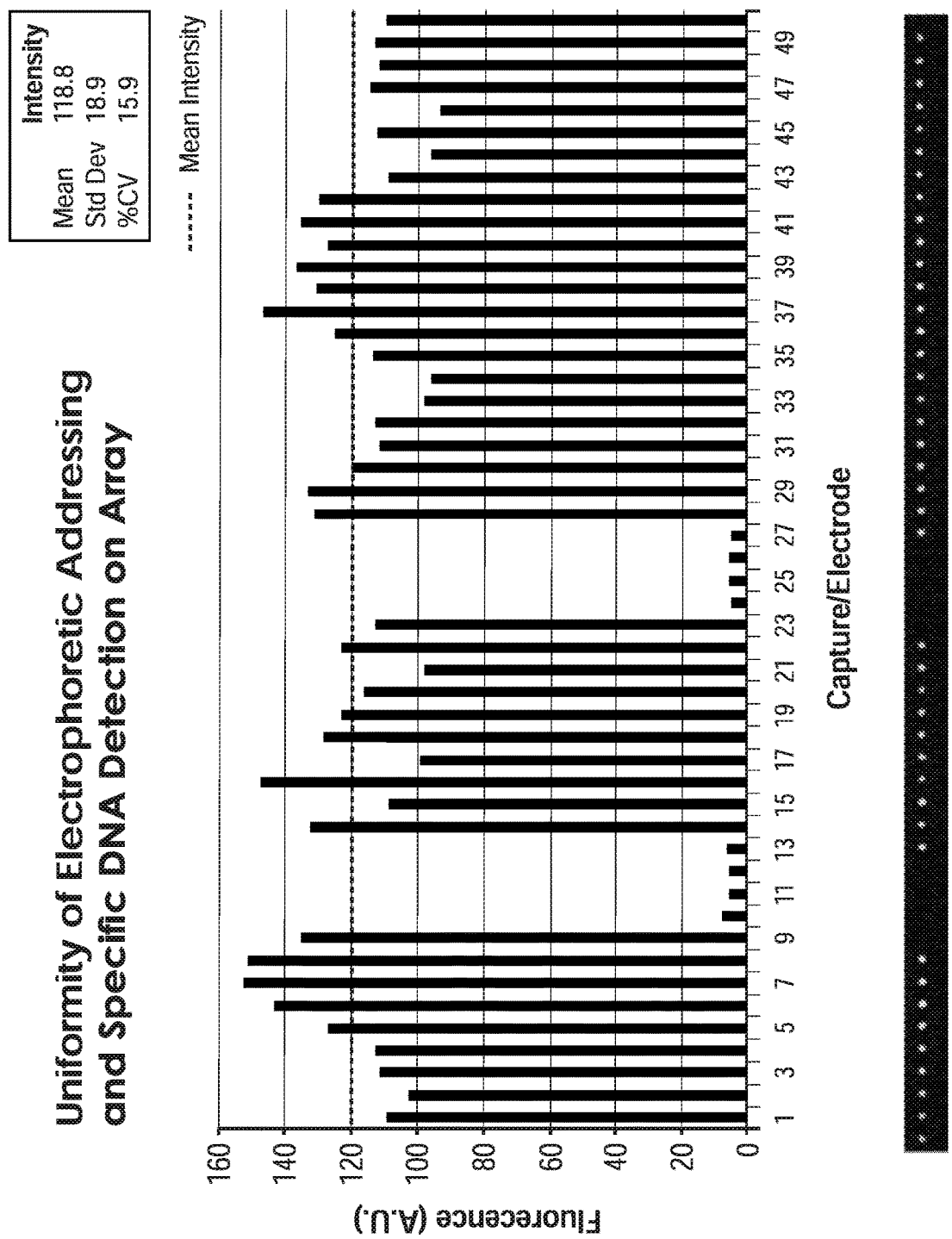
FIG. 16 shows the statistics and obtained quantitative fluorescence data for electrophoretic accumulation of the 55-bp DNA target sequence, detection of its sequence using specific complementary probes embedded within hydrogel covering electrodes of the electrode array and fluorescence image for each electrode spot.

FIG. 16 shows the statistics and obtained quantitative fluorescence data for electrophoretic accumulation of the 55-bp DNA target sequence, detection of its sequence using specific complementary probes embedded within hydrogel covering electrodes of the electrode array and fluorescence image for each electrode spot. Statistical evaluation of the obtained data shows a standard error of about 15% in fluorescence intensity, which is considered very good statistics in measuring fluorescence intensity. Therefore, the preparation of the layered ink structures for the electrode arrays, resistor inks and the entire electrophoretic chip, as well as the assay performance of the chip of the present application seems highly reproducible.

Example 5. Accumulation of the DNA Molecules on the Electrophoretic Chip and Specific Detection of the MS2 Virus Specific DNA recognition sequences were designed within conserved regions of the MS2 virus. An assay consisting of the RNA transcription into the MS2 c-DNA was performed by amplifying the MS2 target using the PCR reaction. The capture probes were designed to be specific for the MS2 DNA target. The test proved reproducibility of the manufacturing process of the electrophoretic chip of the present application.

Figure 17:
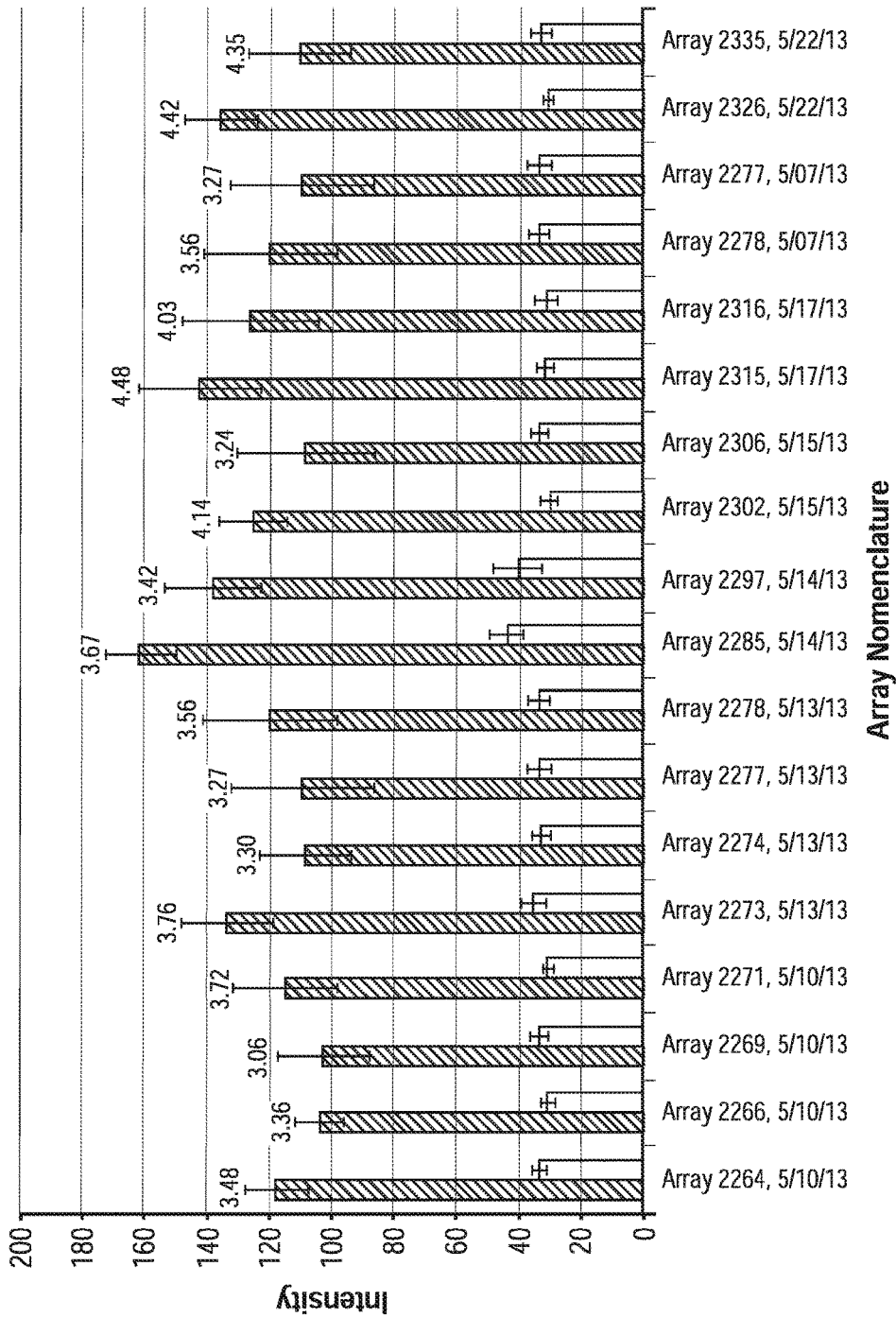
FIG. 17 shows fluorescence data for electrophoretic accumulation and detection of the PCR-amplified DNA MS2 virus target on the electrophoretic chip of the present application.

FIG. 17 shows fluorescence data for electrophoretic accumulation and detection of the PCR-amplified DNA MS2 virus target on the electrophoretic chip disclosed herein. Statistic data for fluorescence intensity (for labels specific/non-specific ratio) obtained for specific detection (blue bars), i.e. target captured on specific probes, versus non-specific probes (red), is shown for a number of assays (each repeated on a new chip prepared according to the same procedure). The standard error obtained for fluorescence measurements on 50 spots for each chip and for the series of chips was around 10%, which clearly demonstrates an excellent reproducibility of the preparation and operation of the electrophoretic chip of the present application for in vitro diagnostics.

Example 6. Accumulation and Detection of Various DNA Sequences

Figure 18A:
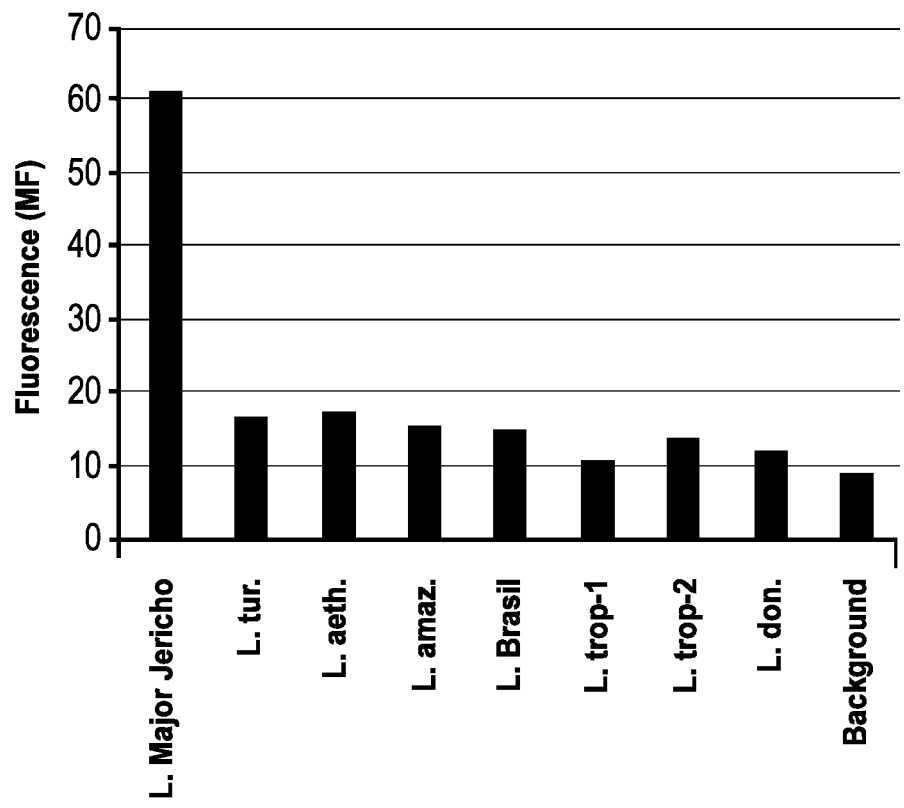
FIGS. 18a-18b show examples of the specific DNA sequence accumulation and detection assays on the electrophoretic chip of the present application.
Figure 18B:
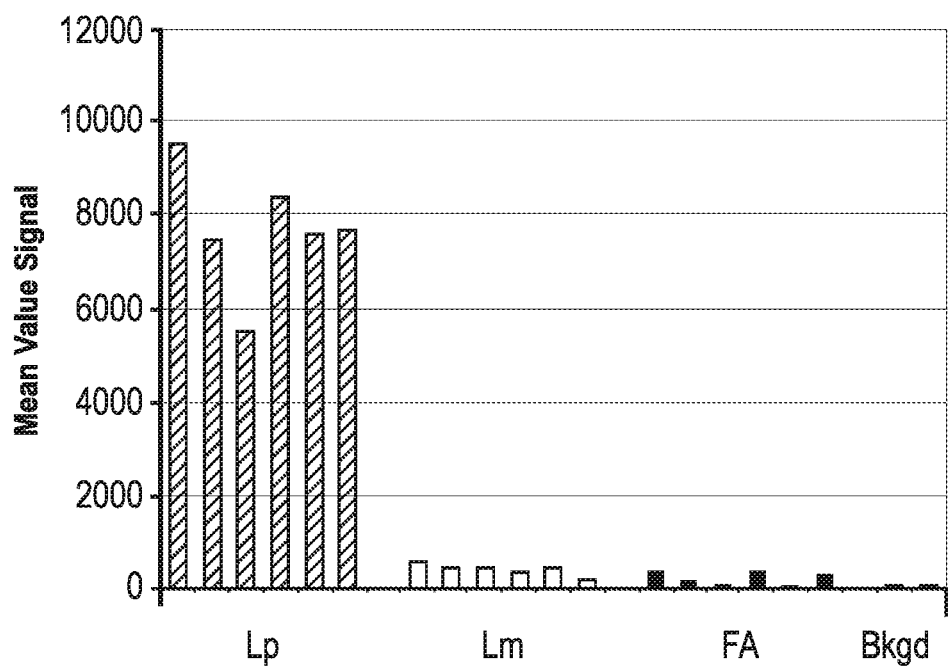

The experiments in this example were carried out with the electrode array chip construction and composition described in Experiment 2 in Table 1 (other configurations exhibited similar positive results). FIGS. 18a and 18b show examples of the specific DNA sequence accumulation and detection assays successfully developed and tested on the electrophoretic chip of the present application. FIG. 18a shows the specific DNA detection and recognition assay for the *Leishmania major* versus other leishmanial subtypes, commonly found in several types of sand flies. FIG. 18b shows the specific DNA identification of *Legionella pneumoniae* as a part of the triplex assay for the community acquired pneumonia assay.

While certain features of the present application have been illustrated and described herein, many modifications, substitutions, changes, and equivalents will be apparent to those of ordinary skill in the art. It is, therefore, to be understood that the appended claims are intended to cover all such modifications and changes as fall within the true spirit of the present application.

The invention claimed is:
1. An electrophoretic chip comprising:
(a) a non-conductive substrate designed to support elements of said electrophoretic chip;
(b) an electrode structure for conducting electric current through said electrophoretic chip, printed on said non-conductive substrate and comprising a counter electrode and at least one working electrode, each of said counter electrode and said at least one working electrode comprising:
  (1) a conductive low-resistance ink layer printed on the non-conductive substrate; and
  (2) a carbon ink layer printed on top of said conductive low-resistance ink layer;
(c) a dielectric ink insulator layer placed on top of, and covering, said electrode structure, said dielectric ink insulator layer having at least one opening above the counter electrode and at least one opening above said at least one working electrode, thereby forming at least one addressable location; and
(d) a molecule capturing matrix spotted on and covering said at least one addressable location, thereby creating at least one microgel region.

2. The electrophoretic chip of claim 1, wherein each one of said addressable locations, upon applying voltage to the electrophoretic chip, receives approximately equal and uniform electric current.

3. The electrophoretic chip of claim 2, wherein said molecule capturing matrix creates at least two microgel regions, such that the adjacent microgel regions are not in direct contact with each other.

4. The electrophoretic chip of claim 2, wherein said molecule capturing matrix is capable of capturing or accumulating molecules at said addressable locations.

5. The electrophoretic chip of claim 4, wherein said molecule capturing matrix comprises a porous polymeric structure, film forming lattice, proteinaceous mixture such as photo-formable proteinaceous mixture, semipermeable solid film, or gas permeable membrane functionalised with chemical functional groups capable of forming an attachment layer.

6. The electrophoretic chip of claim 5, wherein said molecule capturing matrix further comprises at least one separate layer.

7. The electrophoretic chip of claim 2, wherein said at least one microgel region, upon applying voltage to said electrophoretic chip, is capable of promoting an electrophoretic transport of molecules.

8. The electrophoretic chip of claim 1, wherein said molecule capturing matrix creates at least two microgel regions, such that the adjacent microgel regions are not in direct contact with each other.

9. The electrophoretic chip of claim 1, wherein said molecule capturing matrix is capable of capturing or accumulating molecules at said addressable locations.

10. The electrophoretic chip of claim 9, wherein said molecule capturing matrix comprises a porous polymeric structure, film forming lattice, proteinaceous mixture such as photo-formable proteinaceous mixture, semipermeable solid film, or gas permeable membrane functionalised with chemical functional groups capable of forming an attachment layer.

11. The electrophoretic chip of claim 10, wherein said molecule capturing matrix further comprises at least one separate layer.

12. The electrophoretic chip of claim 11, wherein said separate layer is an attachment layer for attaching capture molecules capable of binding a target molecule.

13. The electrophoretic chip of claim. 12, wherein said attachment layer comprises functional groups or chemical moieties for direct binding of said target molecule or for binding said capture molecules.

14. The electrophoretic chip of claim 1, wherein said at least one microgel region, upon applying voltage to said electrophoretic chip, is capable of promoting an electrophoretic transport of molecules.

15. The electrophoretic chip of claim 1. further comprising capture molecules attached to or embedded within said molecule capturing matrix, or attached to the carbon ink layer of said at least one working electrode at the addressable location, said capture molecules being capable of binding a target molecule.

16. The electrophoretic chip of claim 1, further comprising a high-conductivity ink heater layer printed on the bottom side of the non-conductive substrate.

17. The electrophoretic chip of claim 1, further comprising a high- conductivity ink heater layer printed on the top of the non-conductive substrate and is not in contact with the electrode structure.

18. The electrophoretic chip of claim 1. further comprising a thick insulating layer of dielectric or bonded perforated substrate placed on top of said electrophoretic chip, and a cover for covering said dielectric or bonded perforated substrate, wherein said dielectric or bonded perforated substrate comprises a functional fluidic chamber or channel.

19. An electrophoretic device comprising an electrophoretic chip of claim 1, a fluid inlet and outlet, a fluid driver, and a reader.

20. A method for electrophoretic accumulation and detection of at least one analyte in a solution, comprising the steps of (i) applying said solution to the electrophoretic chip of claim 1; (ii) applying voltage to the electrophoretic chip thereby accumulating molecules of said at least one analyte at said at least one addressable location; (iii) removing free (not bound) molecules of said at least one analyte from the solution; and (iv) detecting the presence of the accumulated molecules of said at least one analyte at said at least one addressable location.

* * * * *